US005645829A

United States Patent [19]
Shockley et al.

[11] Patent Number: 5,645,829
[45] Date of Patent: Jul. 8, 1997

[54] MESOTHELIAL CELL GENE THERAPY

[75] Inventors: Ty Robert Shockley, Highland Park, Ill.; Robert William Jackman; Janice Ann Nagy, both of Brookline, Mass.

[73] Assignee: Beth Israel Hospital Association, Brookline, Mass.

[21] Appl. No.: 80,474

[22] Filed: Jun. 18, 1993

[51] Int. Cl.$^6$ .............................. C12N 15/00; C12N 5/00; A61K 48/00; A01N 63/00

[52] U.S. Cl. ................... 424/93.21; 424/572; 435/172.3; 435/371; 435/366; 514/44; 935/62; 935/70; 935/71

[58] Field of Search ............................. 435/172.3, 240.2; 424/93.21, 240.2, 172.3; 935/62, 70, 71

[56] References Cited

U.S. PATENT DOCUMENTS

| | | |
|---|---|---|
| 4,885,238 | 12/1989 | Reddel et al. . |
| 5,399,346 | 3/1995 | Anderson et al. ................ 424/93.21 |

FOREIGN PATENT DOCUMENTS

| | | |
|---|---|---|
| 91/06309 | 5/1991 | Canada . |
| 91/15501 | 10/1991 | Canada . |
| 1298220 | 3/1992 | Canada . |
| 92/11359 | 7/1992 | Canada . |
| 92/12258 | 7/1992 | Canada . |
| 4001319 | 7/1991 | Germany . |
| 4011100 | 10/1991 | Germany . |
| 4123629 | 2/1992 | Germany . |
| 8903994 | 5/1989 | WIPO . |
| WO90/06997 | 6/1990 | WIPO . |
| 91/15580 | 10/1991 | WIPO . |
| 92/05262 | 4/1992 | WIPO . |
| 92/06180 | 4/1992 | WIPO . |
| WO92/15676 | 9/1992 | WIPO . |
| WO93/03769 | 3/1993 | WIPO . |

OTHER PUBLICATIONS

Palmer et al., Blood 73 (2) : 438–445 (1989).

Brody S. and R. Crystal, Adenovirus–mediated in vivo gene transfer, Annals of the New York Academy of Sciences, vol. 716, May 31, 1994, pp. 90–103.

Danos, O. et al., Réimplantation de cellules génuétiquement modifées dans des néo–organes vascularisés, Medicine Sciences, vol. 9, No. 2, Feb. 1993, pp. 208–210.

Nagy, J.A. et al., Mesothelial cell gene therapy, Journal of Cellular Biochemistry, Supplement 18A, Jan., 1994, p. 244.

Setoquchi Y. et al., In vivo gene therapy targeting the peritoneum for $\alpha_1$–antitrypsin deficiency, Americal Review of Respiratory Diseases, vol. 147, No. 4, Apr., 1993, p. A546.

Setoguchi Y. et al., Stimulation of erythropoieses by in vivo gene therapy: physiologic consequence of transfer of the human erythropoietin gene to experimental animals using an adenovirus vector, Clinical Research, vol. 41, No. 2, Apr., 1993, p. 259A.

Brody, S. et al., In–vivo gene transfer to malignant mesothelioma using an adenovirus vector, 1992 International Conference of the American Lung Association and the American Thoracic Society, Miami Beach, FL, May 17–20, 1992, Am. Rev. Respir Dis 145 (4 part 2) 1992, A425.

Rosenberg, S.A., et al., New Eng. J. Med., 323:570–578 (1990), "Gene Transfer Into Humans —Immunotherapy of Patients With Advanced Melanoma, Using Tumor–Infiltrating Lymphocytes Modified By Retroviral Gene Transduction".

Anderson, W.F., Human Gene Therapy 2:99–100 (1991), Editorial "Steady Progress".

Anderson, W.F., "Human Gene Therapy", Science 256:808–813 (1992).

Miller, A.D., "Human gene therapy comes of age", Nature 357:455–460 (1992).

Felgner, P.L. and Rhodes, G., Nature 349:351–352 (1991), "Gene Therapeutics".

DiPaolo, N., Perit. Dial. Int. 9:151–153 (1989), Editorial "The Peritoneal Mesothelium: An Excretory Organ".

Dobbie, J.W., Perit. Dial. Int. 8:3–6 (1988), Editorial "From Philosopher to Fish: The Comparative Anatomy of the Peritoneal Cavity as an Excretory Organ and its Significance for Peritoneal Dialysis in Man".

DiPaolo, N., et al., "Implant of autologous mesothelial cells in animals and a peritoneal dialysis patient", Int. J. Art. Org. 12:485–501 (1989).

DiPaolo, N., et al, "Autologous implant of peritoneal mesothelium in rabbits and man", Clinical Nephrol 34:179–184 (1990).

DiPaolo, N., et al., "Autologous Peritoneal Mesothelial Cell Implant in Rabbits and Peritoneal Dialysis Patients", Nephron 57:323–331 (1991).

Stylianou E., et al., "Isolation, culture and characterization of human peritoneal mesothelial cells", Kidney Intl. 37:1563–1570 (1990).

Pronk, A., et al., In Vitro Cell. Dev. Biol. 29A:127–134 (1993), "A Cobblestone Cell Isolated From The Human Omentum: The Mesothelial Cell; Isolation, Identification, And Growth Characteristics".

Roemer, K. and Friedmann, T., "Concepts and strategies for human gene therapy", Eur. J. Biochem. 208:211–225 (1992).

Brash D.E. et al., Molec. Cell. Biol. 7:2031–2034 (1987), "Strontium Phosphate Transfection of Human Cells in Primary Culture: Stable Expression of the Simian Virus 40 Large–T–Antigen Gene in Primary Human Bronchial Epithelial Cells".

(List continued on next page.)

*Primary Examiner*—Jasemine C. Chambers
*Attorney, Agent, or Firm*—Wolf, Greenfield & Sacks, P.C.

[57] ABSTRACT

Methods and pharmaceutical compositions for modifying the mesothelial cells of a mammalian recipient in situ are provided. The methods include forming a mesothelial cell expression system in vivo or ex vivo and administering the expression system to the mammalian recipient (by way of the body cavities normally lined by mesothelial cells). The mesothelial cell expression system is useful for the localized and systemic delivery of therapeutic agents in situ.

25 Claims, 2 Drawing Sheets

OTHER PUBLICATIONS

Lechner et al., Proc. Natl. Acad. Sci. U.S.A. 82:3884–3888 (1985) "Asbestos–associated chromosomal changes in human mesothelial cells".

Yang Ke, et al., "Establisment of a Human In Vitro Mesothelial Cell Model System for Investigating Mechanisms of Asbestos–Induced Mesothelioma", Amer. J. Pathology 134:979–991 (1989).

Rheinwald, J., et al., Neoplastic Transformation in Human Cell Culture, Eds: J.S. Rhim and A. Dritschilo, The Humana Press, Inc. Totowa, N.J. (1991), "Mitogen–Independence and Autocrine Growth Factor Secretion Displayed by Human Mesothelioma Cells and Oncogene–Transfected Mesothelial Cells".

Temin, H., "Retrovirus vectors for gene transfer," Gene Transfer, Kucherlapati R., Ed., pp. 149–187, Plenum (1986).

Aronson, J.F., et al., Lab. Invest. 34:529–536 (1976), "Initiation of Lung Cell Proliferation by Trypsin".

Esperanca, M.J. and Collins, D.L., J. Ped. Surg. 1:162–169 (1966) "Peritoneal Dialysis Efficiency in Relation to Body Weight".

Rubin, B.J., et al., Am. J. Med. Sci. 295:453–458 (1988), "Measurements of Peritoneal Surface Area in Man and Rat".

Larrick, J.W. and Burck, K.L., Gene Therapy Application of Molecular Biology, Elsevier Science Publishing Co., Inc., New York, pp. 71–104 (1991), "Gene Transfer: Introduction of DNA into Cells Using Physical and Biological Methods".

Rosenfeld, M.A., et al., Science 252:431–434 (1991), "Adenovirus–Mediated Transfer of a Recombinant $\alpha 1$–Antitrypsin Gene to the Lung Epithelium in Vivo".

Hjelle, J.T. et al., Peritoneal Dialysis International, vol. 9, pp. 341–347, 1989, "Isolation and Propagation in Vitro of Peritoneal Mesothelial Cells".

Heldin, P., Biochem J. 283:165–170 (1992), "Characterization of the molecular mechanism involved in the activation of hyaluronan synthetase by platelet–derived growth factor in human mesothelial cells".

Price, J. et al., Proc. Natl. Acad. Sci. USA 84:156–160 (1987), "Lineage analysis in the vertebrate nervous system by retrovirus–mediated gene transfer".

Riese K.H., et al., Path, Res. Pract. 162:327–336 (1978).

Chung–Welch, N., et al., Differentiation 42:44–53 (1989), "Phenotypic comparison between mesothelial and microvascular endothelial cell lineages using conventional endothelial cell markers, cytoskeletal protein markers and in vitro assays of angiogenic potential".

Wu. Y.J., et al., Cell 31:693–703 (1982), "The Mesothelial Keratins: A New Family of Cytoskeletal Proteins Identified in Cultured Mesothelial Cells and Nonkeratinizing Epithelia".

Blaese, R. Mchael, "Progress toward Gene Therapy", Clinical Immunlogy and Immunopathology 61, S47–S55 (1991).

Rheinwald, J.G., Baserga, R., Editor, Cell Growth and Division: a practical approach, IRL Press, Oxford England, pp. 81–94 (1989), "Methods for clonal growth and serial cultivation of normal human epidermal keratinocytes and mesothelial cells".

Bull., H.A., et al., "Effects of autologous mesothelial cell seeding on prostacyclin production within Dacron arterial prostheses," Br. J. Surg., vol. 75, 671–674, Jul. 1988.

Kay, Mark A., et al., "Human gene therapy: present and future", Breast Cancer Research and Treatment 21:83–93, 1992.

Rheinwald, J., et al., "Mitogen–Independance And Autocrine Growth Factor Secretion Displayed by Human Mesothelioma Cells And Oncogene–Transfected Mesothelial Cells", pp. 359–366.

Reddel, R., et al., "Tumorigenicity of Human Mesothelial Cell Line Transfected With EJ–ras Oncogene", vol. 81, No. 12, Jun. 21, 1989, pp. 945–948.

Luzzatto, L., Journal of Internal Medicine, 1992:231:3–6, "Frontiers in medicine Gene transfer and gene therapy".

Hazel C., et al., Dept. of Anatomy, McGill University, Montreal, Canada, "A Technique For the Preparation of Monolayers of Mesothelium".

Watters, W.B., et al., "Virchows Arch. Abt. B. Zellpath. 13, 48–54 (1973), Mitotic Activity of Peritoneum in Contact with a Regenerating Area of Peritoneum".

MESOTHELIAL CELL GENE THERAPY

FIELD OF THE INVENTION

This invention relates to gene therapy. More specifically, the present invention relates to mesothelial cell gene therapy in humans and animals.

BACKGROUND OF THE INVENTION

Gene transfer is now widely recognized as a powerful tool for analysis of biological events and disease processes at both the cellular and molecular level (Murray, E. J., ed. *Methods in Molecular Biology*, Vol. 7, Humana Press Inc., Clifton, N.J., (1991); Kriegler, M., *A Laboratory Manual*, W. H. Freeman and Co., New York (1990)). More recently, the application of gene therapy for the treatment of human diseases, either inherited (e.g., ADA deficiency) or acquired (e.g., cancer or infectious disease), has received considerable attention (Mulligan, R. C., *Science* 260: 926–932 (1993), Tolstoshev, P., *Annu. Rev. Pharmacol. Toxicol.* 32: 573–596 (1993), Miller, A. D., *Nature* 357: 455–460 (1992), Anderson, W. F., *Science* 256: 808–813 (1992), and references therein). With the advent of improved gene transfer techniques and the identification of an ever expanding library of "defective gene"-related diseases, gene therapy has rapidly evolved from a treatment theory to a practical reality.

Traditionally, gene therapy has been defined as "a procedure in which an exogenous gene is introduced into the cells of a patient in order to correct an inborn genetic error" (Blaese, R. M., *Clin. Immunol. Immunopath.* 61: S47–S55 (1991)). Although more than 4500 human diseases are currently classified as genetic, (Roemer, K. and Friedmann, T., *Eur. J. Biochem.* 208: 211–225 (1992) and references cited therein), specific mutations in the human genome have been identified for relatively few of these diseases. Until recently, these rare genetic diseases represented the exclusive targets of gene therapy efforts. Accordingly, most of the N.I.H. approved gene therapy protocols to date have been directed toward the introduction of a functional copy of a defective gene into the somatic cells of an individual having a known inborn genetic error (Miller, A. D., *Nature* 357: 455–460 (1992)). Only recently, have researchers and clinicians begun to appreciate that most human cancers, certain forms of cardiovascular disease, and many degenerative diseases also have important genetic components, and for the purposes of designing novel gene therapies, should be considered a "genetic disorders" (Roemer, K. and Friedmann, T., 1992, supra.). Therefore, gene therapy has more recently been broadly defined as "the correction of a disease phenotype through the introduction of new genetic information into the affected organism" (Roemer, K. and Friedmann, T., 1992, supra.).

Two basic approaches to gene therapy have evolved: (1) ex vivo gene therapy and (2) in vivo gene therapy. In ex vivo gene therapy, cells are removed from a subject and cultured in vitro. A functional replacement gene is introduced into the cells (transfection) in vitro, the modified cells are expanded in culture, and then reimplanted in the subject. These genetically modified, reimplanted cells are reported to secrete detectable levels of the transfected gene product in situ (Miller, A. D., *Blood* 76: 271–278 (1990)); Selden, R. F., et al., *New Eng. J. Med.* 317: 1067–1076 (1987)). The development of improved retroviral gene transfer methods (transduction) has greatly facilitated the transfer into and subsequent expression of genetic material by somatic cells (Cepko, C. L., et al., *Cell* 37: 1053–1062 (1984). Accordingly, retrovirus-mediated gene transfer has been used in clinical trials to mark autologous cells and as a way of treating genetic disease (Rosenberg, S. A., et al., *New Eng. J. Med.* 323: 570–578 (1990); Anderson, W. F., *Human Gene Therapy* 2: 99–100 (1991)). Several ex vivo gene therapy studies in humans have already begun (reviewed in Anderson, W. F., *Science* 256: 808–813 (1992) and Miller A. D., *Nature* 357: 455–460 (1992)).

In in vivo gene therapy, target cells are not removed from the subject. Rather, the transferred gene is introduced into cells of the recipient organism in situ, that is, within the recipient. In vivo gene therapy has been examined in several animal models (reviewed in Felgner, P. L. and Rhodes, G., *Nature* 349: 351–352 (1991)). Several recent publications have reported the feasibility of direct gene transfer in situ into organs and tissues such as muscle (Ferry, N., et al., *Proc. Natl. Acad. Sci* 88: 8377–8781 (1991); Quantin, G., et al., *Proc. Natl. Acad. Sci. USA* 89: 2581–2584 (1992)), hematopoietic stem cells (Clapp, D. W., et al., *Blood* 78: 1132–1139 (1991)), the arterial wall (Nabel, E. G., et al., *Science* 244: 1342–1344 (1989)), the nervous system (Price, J. D., et al., *Proc. Natl. Acad. Sci.* 84: 156–160 (1987)), and lung (Rosenfeld, M. A., et al., *Science* 252: 431–434 (1991)). Direct injection of DNA into skeletal muscle (Wolff, J. A., et al., *Science* 247: 1465–1468 (1990)), heart muscle (Kitsis, R. N., et al., *Proc. Natl. Acad. Sci. USA* 88: 4138–4142 (1991)) and injection of DNA-lipid complexes into the vasculature (Lim, C. S., et al., *Circulation* 83: 2007–2011 (1991); Ledere, G. D., et al., *J. Clin. Invest.* 90: 936–944 (1992); Chapman, G. D., et al., *Circ. Res.* 71: 27–33 (1992)) also has been reported to yield a detectable expression level of the inserted gene product(s) in vivo.

It was initially assumed that hematopoietic stem cells would be the primary target cell type used for ex vivo human gene therapy (see e.g., Wilson, J. M., et al., *Proc. Natl. Acad. Sci* 85: 3014–3018 (1988)), in part, because of the large number of genetic diseases associated with differentiated stem cell lineages (Miller, D., *Nature* 357: 455–460 (1992)). However, because of problems inherent to hematopoietic stem cell transfection (e.g., inefficient transgene expression) (Miller, A. D., *Blood* 76: 271–278 (1990)), more recent gene therapy efforts have been aimed at the identification of alternative cell types for transformation. These include: keratinocytes (Morgan, J. R., et al., *Science* 237: 1476–1479 (1987)), fibroblasts (Palmer, T. D., et al., *Proc. Natl. Acad. Sci.* 88: 1330–1334 (1991); Garver Jr., R. I., et al., *Science* 237: 762–764 (1987); International Patent Application PCT/US92/01890, having publication number WO 92/15676), lymphocytes (Reimann, J. K., et al., *J. Immunol. Methods* 89: 93–101 (1986)), myoblasts (Barr, E. and Leiden, J. M., *Science* 254: 1507–1509 (1991); Dai, Y. et al., PNAS 89: 10892–10895 (1992); Roman, M., et al., *Somatic Cell and Molecular Genetics* 18: 247–258 (1992)), smooth muscle cells (Lynch, C. M. et al., *Proc. Natl. Acad. Sci. USA* 89: 1138–1142 (1992), and endothelial cells (Nabel, E. G., et al., *Science* 244: 1342–1344 (1989), International Patent Application PCT/US89/05575, having publication number WO 90/06997), the contents of which references and patent/patent applications are incorporated herein by reference.

Despite the wide range of cell types tested, a satisfactory target cell for human gene therapy has not yet been identified. The inadequacies of the above-identified cell types include: (1) inefficient (Williams, et al., 1984; Joyner, et al., 1985) or transient (Mulligan, R. C., *Science* 260: 926–932 (1993)) expression of the inserted gene; (2) potential tumorigenicity of the implanted transduced cell (Selden, et al., 1987; Garver, et al., 1987b); (3) rejection of the implanted genetically modified cell in the absence of harsh immunosuppressive therapy (Selden, et al., 1987); (4) necrosis following subcutaneous injection of cells (Bell, et al., 1983); (5) limited dissemination of the inserted gene product from the site of transduced cell implantation (Morgan, et al., 1987) (see also WO 92/15676); and (6) limitations in the amount of therapeutic agent delivered in situ.

The delivery of a therapeutically effective dose of a therapeutic agent in situ depends on both the efficiency of transfection (or transduction), as well as the number of target cells. Thus, despite the potentially high efficiency of transduction using retroviral vectors, many of the above-described cell types are not satisfactory target cells for in vivo gene therapy because of the relatively small numbers of cells available for transduction in situ. Similarly, many of these cell types are not satisfactory for ex vivo gene therapy because of the limited area available in situ for receiving (e.g., by implantation) the genetically modified cells or because of inherent difficulties in accessing a particular anatomical location for implantation of the genetically modified cells.

Endothelial cell-based gene therapy, in particular, is limited by the relatively small area available in situ for receiving genetically modified endothelial cells. Typically, ex vivo gene therapy using endothelial cells requires that a relatively small portion of a blood vessel be sectioned-off to eliminate blood flow through the vessel before removing cells from, or introducing cells to, the blood vessel (Nabel, E. G., et al., *Science* 244: 1342–1344 (1989); Lim, C. S. et al., *Circulation* 83: 2007–2011 (1991); Chapman, G. D. et al., *Circulation Res.* 71: 27–33 (1992)). Consequently, a relatively small number of genetically modified endothelial cells can be implanted into the target vessel. As a result, the delivery of a therapeutically effective dose of therapeutic agent in situ is limited by the total number of implanted endothelial cells.

SUMMARY OF THE INVENTION

Accordingly, it is an object of the instant invention to provide a new method of gene therapy based on the use of genetically engineered mesothelial cells and to the use thereof for delivering a therapeutic agent to a mammalian recipient.

The ideal ex vivo gene therapy method would use a cell that (1) can be easily isolated from the patient, (2) can be modified in vitro to stably express exogenous genetic material (e.g., a therapeutic agent); (3) can be conveniently implanted in the recipient; (4) is non-thrombogenic; and (5) can be implanted into the recipient in large numbers. The ideal in vivo gene therapy method would use a cell that (1) is present in the recipient in large numbers and (2) can be modified in situ to stably express exogenous genetic material (e.g., a therapeutic agent). Preferably, the genetically modified cell would include regulatory elements for controlling the amount of therapeutic agent transcribed and/or expressed, as well as additional elements for directing the therapeutic agent to intracellular, extracellular and/or plasma membrane-associated locations. The preferred genetically modified cells would survive and continue to produce the therapeutic agent in a controlled manner in situ for an amount of time necessary for the therapeutic agent to have a beneficial (i.e., therapeutic) effect, without interfering with the normal function of the tissue in which the cells are located.

The instant invention satisfies these and other objects by providing methods for forming a mesothelial cell expression system, the expression system produced thereby and pharmaceutical compositions containing the same. The mesothelial cell expression system expresses exogenous genetic material (e.g., a heterologous gene encoding a therapeutic agent) and is useful as a vehicle for delivering the gene product to the mammalian recipient in .situ. In a preferred embodiment, the mammalian recipient is a human.

In general, the invention relates to genetically engineered mesothelial cells and the use thereof for expressing a therapeutic agent. More particularly, the invention relates to a method for gene therapy which is capable of both localized and systemic delivery of a therapeutically effective dose of a therapeutic agent. Thus, the invention provides a method for delivering a therapeutically effective amount of a therapeutic agent to any coelomic (pericardial, pleural, and peritoneal) cavity, and subsequently to the systemic circulation by virtue of draining lymphatics, in direct communication with the systemic circulation. Thus, a mesothelial cell expression system is useful for delivering a therapeutic agent throughout the whole patient by, first, the delivery of a therapeutic agent in situ (e.g., to the patient's peritoneal cavity) and then to the systemic circulation of the patient via the interconnecting lymphatic network.

According to one aspect of the invention, a mesothelial cell expression system for expressing a therapeutic agent in a mammalian recipient is provided. The expression system (also referred to herein as a "genetically modified mesothelial cell") comprises a mesothelial cell and an expression vector for expressing the therapeutic agent. Expression vectors of the instant invention include, but are not limited to, viruses, plasmids, and other vehicles for delivering heterologous genetic material to a mesothelial cell. Accordingly, the term "expression vector" as used herein refers to a vehicle for delivering heterologous genetic material to a mesothelial cell.

Preferably, the expression vector further includes a promoter for controlling transcription of the heterologous gene. More preferably, the promoter is an inducible promoter (described below). The expression system is suitable for administration to the mammalian recipient. In a preferred embodiment, the expression system comprises a plurality of non-immortalized mesothelial cells, each cell containing at least one recombinant gene encoding at least one therapeutic agent.

The mesothelial cell expression system can be formed ex vivo or in vivo. To form the expression system ex vivo, one or more isolated mesothelial cells are transduced with a virus or transfected with a nucleic acid or plasmid in vitro. Preferably the transduced or transfected mesothelial cells are thereafter expanded in culture and thereafter administered to the mammalian recipient for delivery of the therapeutic agent in situ. In a preferred embodiment, the mesothelial cell comprises an autologous cell, i.e., the cell is isolated from the mammalian recipient. The genetically modified cell(s) are administered to the recipient by, for example, implanting the cell(s) or a graft (or capsule) including a plurality of the cells into a mesothelial cell-compatible site of the recipient. Representative mesothelial cell-compatible sites include, for example, the peritoneal, pleural and pericardial cavities. Preferably, the mesothelial cell-compatible site is denuded, i.e., a section of mesothelial cells is removed, to expose the underlying basement membrane, prior to implanting the genetically modified cells.

According to yet another aspect of the invention, a method for genetically modifying the mesothelial system of a mammalian recipient (preferably a human) in vivo is provided. The method comprises introducing an expression vector for expressing a heterologous gene product into a mesothelial cell of the patient in situ. To form the expression system in vivo, an expression vector for expressing the therapeutic agent is introduced in vivo into a coelomic cavity (e.g., peritoneal cavity) of the mammalian recipient by, for example, intraperitoneal injection.

Preferably, the expression vector for expressing the heterologous gene includes an inducible promoter for controlling transcription of the heterologous gene product. Accordingly, delivery of the therapeutic agent in situ is controlled by exposing the cell in situ to conditions which induce transcription of the heterologous gene.

In the preferred embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material which has a beneficial effect on the mammalian recipient. Thus, "therapeutic agent" embraces both therapeutic and prophylactic molecules having nucleic acid (e.g., antisense RNA) and/or protein components.

According to one preferred embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition. Thus, exemplary therapeutic agents (with the conditions they treat appearing in the parentheses) include Factor VIII (hemophilia A) and Factor IX (hemophilia B), adenosine deaminase (severe combined immunodeficiency disease), erythropoietin (anemia), and tumor necrosis factor (cancer). Lists of these and other therapeutic agents are provided in Tables 1–3. Exemplary therapeutic agents that are prophylactic agents for treating a prophylactic process (with their use appearing in parentheses) include thyroxine (for treating hypothyroidism), estrogen/progesterone (as contraceptive agents), albumin (as an oncotic agent in peritoneal dialysis).

According to yet another embodiment, a pharmaceutical composition is disclosed. The pharmaceutical composition comprises a plurality of the above-described genetically modified mesothelial cells and a pharmaceutically acceptable carrier. Preferably, the pharmaceutical composition is for treating a condition amenable to gene replacement therapy and the exogenous genetic material comprises a heterologous gene encoding a therapeutic agent for treating the condition. More preferably, the pharmaceutical composition contains an amount of genetically modified cells sufficient to deliver a therapeutically effective dose of the therapeutic agent to the patient. Exemplary conditions amenable to gene replacement therapy are described below.

According to another aspect of the invention, a method for forming the above-described pharmaceutical composition is provided. The method includes introducing an expression vector for expressing a heterologous gene product into a mesothelial cell to form a genetically modified mesothelial cell and placing the genetically modified cell in a pharmaceutically acceptable carrier.

According to still another aspect of the invention, a mesothelial cell graft is disclosed. The graft comprises a plurality of genetically modified mesothelial cells attached to a support which is suitable for implantation into the mammalian recipient. The support may be formed of a natural or synthetic material. According to one embodiment, the mesothelial cell graft comprises a patch of peritoneum including a plurality of mesothelial cells, which cells contain a recombinant gene. In a preferred embodiment, the cells are genetically modified ex vivo following excision of the patch from the mammalian recipient.

According to still another aspect of the invention, an encapsulated mesothelial cell expression system is disclosed. The encapsulated expression system comprises a plurality of genetically modified mesothelial cells contained within a capsule which is suitable for implantation into the mammalian recipient. The capsule may be formed of a natural or synthetic material. Preferably, the capsule containing the plurality of genetically modified mesothelial cells is implanted in the peritoneal cavity.

These and other aspects of the invention as well as various advantages and utilities will be more apparent with reference to the detailed description of the preferred embodiments and to the accompanying drawings.

DESCRIPTION OF THE PREFERRED EMBODIMENTS

Figure 1:
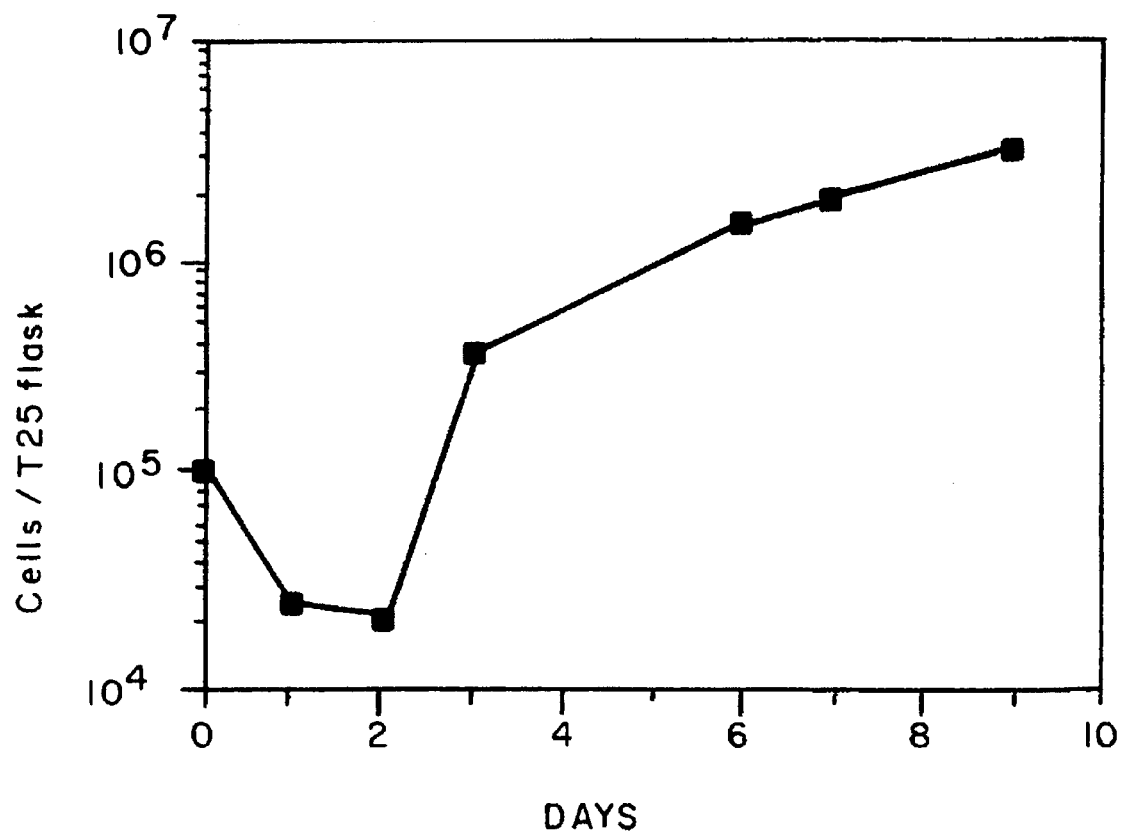
FIG. 1 a growth curve of rat primary mesothelial cells in vitro.

The instant invention provides a mesothelial cell expression system for expressing exogenous genetic material in a mammalian recipient. The expression system, also referred to as a "genetically modified mesothelial cell", comprises a mesothelial cell and an expression vector for expressing the exogenous genetic material. The genetically modified mesothelial cells are suitable for administration to a mammalian recipient, where they replace the endogenous mesothelial cells of the recipient. Thus, the preferred genetically modified cells are non-immortalized and are non-tumorigenic.

The mesothelial cells of the instant invention are parietal, visceral surface or free-floating mesothelial cells that are present in, or derived from, a simple squamous epithelium that forms the limiting serosal membranes that line the coelomic cavities (i.e., pleural, pericardial, and peritoneal cavities) (reviewed in (Whitaker, D., et al., *CRC Critical Reviews in Toxicology* 10: 81–144 (1982); Dobbie, J. W., *Am. J. Kid. Dis* 15: 97–109 (1990); Gotloib, L. and Shostak, A., *Peritoneal Dialysis*, K. D. Nolph, Editor, Nijhoff, Amsterdam: 67–95 (1989)). Mesothelial cells function by providing a frictionless surface which facilitates movement within the pleural, pericardial, and peritoneal cavities (Whitaker, D., et al. supra). In addition, the mesothelial cells possess a secretory function (Di Paolo, N., Perit. Dial. Int. 9: 151–153 (1989); Dobbie, J. W., Perit. Dial. Int. 8: 3–6 (1988)) and by virtue of their anatomical location in the peritoneal cavity, are amenable to removal and subsequent reimplantation (Di Paolo, N., et al., Int. J. Art. Org. 12: 485–501 (1989); Di Paolo, N., et al., Clinical Nephrol. 34: 179–1848 (1990); Di Paolo, N., et al., Nephron 57: 323–331 (1991)).

According to one embodiment, the mesothelial cells are transformed or otherwise genetically modified ex vivo. The mesothelial cells are isolated from a mammal (preferably a human), transformed (i.e., transduced or transfected in vitro) with a vector for expressing a heterologous (e.g., recombinant) gene encoding the therapeutic agent, and then administered to a mammalian recipient for delivery of the therapeutic agent in situ. Preferably, the mammalian recipient is a human and the mesothelial cells to be modified are autologous cells, i.e., the cells are isolated from the mammalian recipient. The isolation and culture of mesothelial cells in vitro has been reported (see e.g., Stylianou, E., et al., Kidney Intl. 37: 1563–1570 (1990); Pronk, A. et al. In Vitro Cell. Dev. Biol. 29A: 127–134 (1993)), as has the implantation of autologous peritoneal mesothelial cells in peritoneal dialysis patients (see e.g., Di Paolo, N., et al., Nephron. 57: 323–331 (1991) and references cited therein).

According to another embodiment, the mesothelial cells are transformed or otherwise genetically modified in vivo. The mesothelial cells from the mammalian recipient (preferably a human), are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in mesothelial cells; or if it is naturally found in the cells, it is not transcribed or expressed at biologically significant levels by mesothelial cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring mesothelial cell). To illustrate, a synthetic or natural gene encoding human erythropoietin (EPO) would be considered "exogenous genetic material" with respect to human peritoneal mesothelial cells since the latter cells do not naturally express EPO; similarly, a human interleukin-1 gene inserted into a peritoneal mesothelial cell would also be an exogenous gene to that cell since peritoneal mesothelial cells do not naturally express interleukin-1 at biologically significant levels. Still another example of "exogenous genetic material" is the introduction of only part of a gene to create a recombinant gene, such as combining an inducible promoter with an endogenous coding sequence via homologous recombination.

In the preferred embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material which has a beneficial effect on the mammalian recipient. Thus, "therapeutic agent" embraces both therapeutic and prophylactic molecules having nucleic acid (e.g., antisense RNA) and/or protein components.

A number of diseases caused by single-gene defects have been identified (Roemer, K. and Friedmann, T., Eur J. Biochem. 208: 211–225 (1992); Miller, A. D., Nature 357: 455–460 (1992); Larrick, J. W. and Burck, K. L. Gene Therapy. Application of Molecular Biology, Elsevier, N.Y., (1991) and references contained therein). Examples of these diseases, and the therapeutic agents for treating the exemplary diseases, are provided in Table 1.

As used herein, "acquired pathology" refers to a disease or syndrome manifested by an abnormal physiological, biochemical, cellular, structural, or molecular biological state. Exemplary acquired pathologies, and the therapeutic agents for treating the exemplary pathologies, are provided in Table 2.

The condition amenable to gene replacement therapy alternatively can be a genetic disorder or an acquired pathology that is manifested by abnormal cell proliferation, e.g., cancers arising in or metastasizing to the coelomic cavities. According to this embodiment, the instant invention is useful for delivering a therapeutic agent having anti-neoplastic activity (i.e., the ability to prevent or inhibit the development, maturation or spread of abnormally growing cells), to tumors arising in or metastasizing to the coelomic cavities, (e.g., ovarian carcinoma, mesothelioma, colon carcinoma). Therapeutic agents for treating these and other cancers include, for example, the anti-neoplastic agents provided in Table 3.

TABLE 1

Therapeutic Agents for Treating Diseases Involving Single-Gene Defects*

| Disease | Therapeutic Agent |
| --- | --- |
| Immunodeficiency | Adenosine deaminase |
|  | Purine nucleoside phosphorylase |
| Hypercholesterolaemia | LDL receptor |
| Haemophilia A | Factor VIII |
| Haemophiliaa B | Factor IX |
| Gaucher's disease | Glucocerebrosidase |
| Mucopolysaccharidosis | β-glucuronidase |
| Emphysema | $\alpha_1$-antitrypsin |
| Cystic fibrosis | Cystic fibrosis trans-membrane regulator |
| Phenylketonuria | Phenylalanine hydroxylase |
| Hyperammonaemia | Ornithine transcarbamylase |
| Citrullinaemia | Arginosuccinate synthetase |
| Muscular dystrophy | Dystrophin |
| Thalassaemia | β-globin |
| Sickle cell anaemia | α-globin |
| Leukocyte adhesion deficiency | CD-18 |
| von Willebrand's disease | von Willebrand Factor |

*see Roemer, K. and Friedmann, T., Eur J. Biochem. 208:211–225 (1992) and Miller, A. D., 1992, Nature 357:455–460 and references contained therein.

TABLE 2

Therapeutic Agents for Acquired Pathologies

| | Therapeutic Agent |
|---|---|
| Associated with Peritoneal Dialysis | |
| Anemia | Erythropoietin |
| Peritoneal sclerosis | Fibrinolytic agents (e.g., tissue plasminogen activator (t-PA), or single chain urokinase plasminogen activator (scu-PA) |
| Peritonitis | Anti-oxidants (e.g., Superoxide Dismutase, Catalase) |
| Uremia | Urease |
| Other Conditions | |
| Septic Shock | Anti-thrombotic agents (e.g., elastase-resistant form of thrombomodulin (TM)) |
| Diabetes mellitus | Insulin |
| Pituitary Dwarfism | Human growth hormone |
| Thrombosis | Hirudin, secreted form of TM |
| Post-Surgical Adhesions | Anti-thrombotic agents (e.g., thrombomodulin, hirudin) Fibrinolytic agents (e.g., TPA, scu-PA) Surfactants |
| AIDS | CD-4 |

TABLE 3

Therapeutic Agents for Treating Cancers*

| Defective Gene | Therapeutic Agent |
|---|---|
| Oncogenes | corresponding normal genes, oncogene antisense RNA |
| Mutated Tumor-Suppressor genes | Normal Tumor-Suppressor (e.g., p53) |
| Unidentified defect | cytokines, the interferons, tumor necrosis factor, the interleukins. |

*see Roemer, K. and Friedmann, T., 1992, supra., and references contained therein.

Delivery of a therapeutic agent by a genetically modified mesothelial cell is not limited to delivery to the coelomic cavity in which the genetically modified mesothelial cells reside. By virtue of the anatomical location of the coelomic cavities, a therapeutic agent secreted by a genetically modified mesothelial cell within a coelomic cavity could reach the lymphatic network draining that coelomic cavity. Accordingly, the genetically modified mesothelial cells of the invention are useful for delivering a therapeutic agent, such as an anti-neoplastic agent, to the coelomic cavities (e.g., peritoneal, pleural, pericardial), to the lymphatic network into which these cavities drain and to the vascular system via the interconnecting lymphatic network. Therefore a therapeutic agent, such as an anti-neoplastic agent, delivered by genetically modified mesothelial cells, would reach cancer cells within the coelomic cavities, within the draining lymphatics and at distant metastatic sites.

Alternatively, the condition amenable to gene replacement therapy is a prophylactic process, i.e., a process for preventing disease or an undesired medical condition. Thus, the instant invention embraces a mesothelial cell expression system for delivering a therapeutic agent that has a prophylactic function (i.e., a prophylactic agent) to the mammalian recipient. Such therapeutic agents (with the disease or undesired medical condition they prevent appearing in parentheses) include: estrogen/progesterone (pregnancy); thyroxine (hypothyroidsm); and agents which stimulate, e.g., gamma-interferon, or supplement, e.g., antibodies, the immune system response (diseases associated with deficiencies of the immune system).

In summary, the term "therapeutic agent" includes, but is not limited to, the agents listed in Tables 1–3, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent. As will be appreciated by one of ordinary skill in the art, a functionally equivalent proteins can be produced by recombinant techniques, e.g., by expressing a "functionally equivalent DNA". As used herein, the term "functionally equivalent DNA" refers to a non-naturally occurring DNA which encodes a therapeutic agent. For example, many, if not all, of the agents disclosed in Tables 1–3 have known amino acid sequences, which are encoded by naturally occurring nucleic acids. However, due to the degeneracy of the genetic code, more than one nucleic acid can encode the same therapeutic agent. Accordingly, the instant invention embraces therapeutic agents encoded by naturally-occurring DNAs, as well as by non-naturally-occurring DNAs which encode the same protein as encoded by the naturally-occurring DNA.

The above-disclosed therapeutic agents and conditions amenable to gene replacement therapy are merely illustrative and are not intended to limit the scope of the instant invention. The selection of a suitable therapeutic agent for treating a known condition is deemed to be within the scope of one of ordinary skill of the art without undue experimentation.

Methods for Introducing Genetic Material into Mesothelial Cells

The exogenous genetic material (e.g., a cDNA encoding one or more therapeutic proteins) is introduced into the mesothelial cell ex vivo or in vivo by genetic transfer methods, such as transfection or transduction, to provide a genetically modified mesothelial cell. Various expression vectors (i.e., vehicles for facilitating delivery of exogenous genetic material into a target cell) are known to one of ordinary skill in the art.

As used herein, "transfection of mesothelial cells" refers to the acquisition by a mesothelial cell of new genetic material by incorporation of added DNA. Thus, transfection refers to the insertion of nucleic acid into a mesothelial cell using physical or chemical methods. Several transfection techniques are known to those of ordinary skill in the art including: calcium phosphate DNA co-precipitation (Methods in Molecular Biology, Vol. 7, Gene Transfer and Expression Protocols, Ed. E. J. Murray, Humana Press (1991)); DEAE-dextran (supra); electroporation (supra); cationic liposome-mediated transfection (supra); and tungsten particle-facilitated microparticle bombardment (Johnston, S. A., Nature 346: 776–777 (1990)). Strontium phosphate DNA co-precipitation (Brash D. E. et al. Molec. Cell. Biol. 7: 2031–2034 (1987) is the preferred transfection method.

In contrast, "transduction of mesothelial cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced mesothelial cell. A mesothelial cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

U.S. Pat. No. 4,885,238, issued Dec. 5, 1989 to Reddel et al., the contents of which are incorporated herein by reference, discloses immortalized human bronchial epithelial and human mesothelial cell lines. The immortalized cells were prepared by culturing normal human mesothelial (NHM) cells from pleural effusions or ascites fluids as described by Lechner et al, (Proc. Natl. Acad. Sci. U.S.A. 82: 3884-3888, 1985) and thereafter transducing the cultured cells with SV40 virus or with an adenovirus-12 SV40 chimeric virus, or transfecting the cultured cells with a recombinant plasmid containing the Rous sarcoma virus long terminal repeat and the ori-SV40 early region by strontium phosphate co-precipitation (Brash et al.: Molec. Cell. Biol. 7: 2031-20341987). The term "immortalized cell" as used in the Reddel et al., patent, means a cell which grows continually without senescence when cultured in vitro in a suitable growth medium. Accordingly, the transformed mesothelial cells of Reddel et al., are immortalized and are not suitable for direct implantation into a mammalian recipient. Thus, the Reddel et al. cells are limited to a variety of in vitro applications. Immortalized mesothelial cell lines are also disclosed in Yang Ke, et al., Amer. J. Pathology 134: 979-991 (1989), on which reference H. Reddel is a co-author, and Rheinwald, J., et al., Neoplastic Transformation in Human Cell Culture, Eds.: J. S. Rhim and A. Dritschilo, (1991), The Humana Press Inc., Totowa, N.J.).

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. Preferably, the exogenous genetic material is introduced into the mesothelial cell genome immediately downstream from the promoter so that the promoter and coding sequence are operatively linked so as to permit transcription of the coding sequence. A preferred retroviral expression vector includes an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR) (Scharfmann et al., Proc. Natl. Acad. Sci. USA 88: 4626–4630 (1991)), adenosine deaminase, phosphoglycerol kinase (PGK), pyruvate kinase, phosphoglycerol mutase, the β-actin promoter (Lai et al., Proc. Natl. Acad. Sci. USA 86: 10006-10010 (1989)), and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thyroidinc kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified mesothelial cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified mesothelial cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the mesothelial cell; (3) the number of transduced/transfected mesothelial cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified mesothelial cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector preferably includes a selection gene, for example, a neomycin resistance gene, for facilitating selection of mesothelial cells that have been transfected or transduced with the expression vector. Alternatively, the mesothelial cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the the scope of one of ordinary skill in the art without undue experimentation.

The therapeutic agent can be targetted for delivery to an extracellular, intracellular or membrane location. If it is desirable for the gene product to be secreted from the mesothelial cells (e.g., to deliver the therapeutic agent to the lymphatic and vascular systems), the expression vector is designed to include an appropriate secretion "signal" sequence for secreting the therapeutic gene product from the cell to the extracellular milieu. If it is desirable for the gene product to be retained within the mesothelial cell, this secretion signal sequence is omitted. In a similar manner, the expression vector can be constructed to include "retention" signal sequences for anchoring the therapeutic agent within the mesothelial cell plasma membrane. For example, all membrane proteins have hydrophobic transmembrane regions which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

The following discussion is directed to various utilities of the instant invention. For example, the instant invention has utility as an expression system suitable for detoxifying intra- and/or extracellular toxins in situ. By attaching or omitting the appropriate signal sequence to a gene encoding a therapeutic agent capable of detoxifying a toxin, the therapeutic agent can be targeted for delivery to the extracellular milieu, to the mesothelial cell plasma membrane or to an intracellular location. In a preferred embodiment, the exogenous genetic material containing a gene encoding an intracellular detoxifying therapeutic agent, further includes sequences encoding surface receptors for facilitating transport of extracellular toxins into the cell where they can be detoxified intracellularly by the therapeutic agent. Alternatively, the mesothelial cells can be genetically modified to express the detoxifying therapeutic agent anchored within the mesothelial cell plasma membrane such that the active portion extends into the extracellular milieu. The active portion of the membrane-bound therapeutic agent detoxifies toxins which are present in the extracellular milieu. The above-described embodiment can be useful in the treatment of end-stage renal disease patients, who accumulate toxic substances (e.g., beta-2 microglobulin) in their blood. Implantation of genetically modified mesothelial cells expressing a therapeutic agent for detoxifying or removing accumulated toxins could decrease the morbidity associated with these toxins. Other pathologies, and their corresponding detoxifying therapeutic agent(s), for which the above described embodiment would apply include, but are not limited to: hypercholesterolemia (phospholipase $A_2$ or LDL receptor); phenylketonuria (phenylalanine hydroxylase); hyperammonaemia (ornithine transcarbamylase); citrullinaemia (arginosuccinate synthetase); and hyperbilirubinemia (bilirubin decarboxylase) (Robbins, S. L., Cotran, R. S. and Kumar, V., *Pathologic Basis of Disease*, 3rd edition, W. B. Saunders Co., Philadelphia, (1984)).

In addition to the above-described therapeutic agents, some of which are targetted for intracellular retention, the instant invention also embraces agents intended for delivery to the extracellular milieu and/or agents intended to be anchored in the mesothelial cell plasma membrane. For example, expression of an anti-thrombotic agent, such as thrombomodulin, on the surface of a plurality of mesothelial cells implanted onto the peritoneal wall can prevent clotting as well as reduce the incidence of post-surgical adhesions by preventing the deposition of fibrin. Other examples of therapeutic agents suitable for expression on the surface of a genetically modified mesothelial cell include, but are not limited to: LDL receptor; single chain urokinase plasminogen activator (scu-PA); and tissue type plasminogen activator (t-PA).

The selection and optimization of a particular expression vector for expressing a specific gene product in an isolated mesothelial cell is accomplished by obtaining the gene, preferably with one or more appropriate control regions (e.g., promoter, insertion sequence); preparing a vector construct comprising the vector into which is inserted the gene; transfecting or transducing cultured mesothelial cells in vitro with the vector construct; and determining whether the gene product is present in the cultured cells.

In a preferred embodiment, vectors for mesothelial cell gene therapy are viruses, more preferably replication-deficient viruses (described in detail below). Exemplary viral vectors are derived from: Harvey Sarcoma virus; ROUS Sarcoma virus, (MPSV); Moloney murine leukemia virus and DNA viruses (e.g., adenovirus) (Temin, H., "Retrovirus vectors for gene transfer", in *Gene Transfer*, Kucherlapati R, Ed., pp 149–187, Plenum, (1986)).

Replication-deficient retroviruses are capable of directing synthesis of all virion proteins, but are incapable of making infectious particles. Accordingly, these genetically altered retroviral expression vectors have general utility for high-efficiency transduction of genes in cultured cells, and specific utility for use in the method of the present invention. Such retroviruses further have utility for the efficient transduction of genes into mesothelial cells in vivo. Retroviruses have been used extensively for transferring genetic material into cells. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with the viral particles) are provided in Kriegler, M. *Gene Transfer and Expression, A Laboratory Manual*, W. H. Freeman Co, N.Y., (1990) and Murray, E. J., ed. *Methods in Molecular Biology*, Vol. 7, Humana Press Inc., Clifton, N.J., (1991).

The major advantage of using retroviruses for gene therapy is that the viruses insert the gene encoding the therapeutic agent into the host cell genome, thereby permitting the exogenous genetic material to be passed on to the progeny of the cell when it divides. In addition, gene promoter sequences in the LTR region have been reported to enhance expression of an inserted coding sequence in a variety of cell types (see e.g., Hilberg et al., *Proc. Natl. Acad. Sci. USA* 84: 5232–5236 (1987); Holland et al., *Proc. Natl. Acad. Sci. USA* 84: 8662–8666 (1987); Valerio et al., *Gene* 84: 419–427 (1989). The major disadvantages of using a retrovirus expression vector are (1) insertional mutagenesis, i.e., the insertion of the therapeutic gene into an undesirable position in the target cell genome which, for example, leads to unregulated cell growth and (2) the need for target cell proliferation in order for the therapeutic gene carried by the vector to be integrated into the target genome (Miller, D. G., et al., *Mol. Cell. Biol.* 10: 4239–4242 (1990)). While proliferation of the target cell is readily achieved in vitro, proliferation of many potential target cells in vivo is very low.

Despite these apparent limitations, in vivo gene therapy using replication-deficient retroviral vectors to deliver a therapeutically effective amount of a therapeutic agent can be efficacious if the efficiency of transduction is high and/or the number of target cells available for transduction is high. Methods for stimulating mesothelial cell proliferation in vivo have been reported (Aronson, J. F. et al. *Lab. Invest.* 34: 529–536 (1976)) and can be adapted to increase the number of target mesothelial cells in vivo. Accordingly, the potentially large number of mesothelial cells available for in vivo gene therapy, (e.g., ~1 to 4×10$^9$ cells in the adult human, based on the observed confluent cell culture density of ~1 to 3×10$^5$ cells/cm$^2$ and a peritoneal surface area of ~1 m$^2$ (Esperanca, M. J. and Collins, D. L. *J. Ped. Surg.* 1: 162–169 (1966); Rubin, B. J. et al., *Am. J. Med. Sci.* 295: 453–458 (1988)) as well as the large area available for implantation of extracorporeally transformed mesothelial cells (e.g. ~1 m$^2$ in the adult human (Esperanca, M. J. and Collins, D. L. *J. Ped. Surg.* 1: 162–169 (1966); Rubin, B. J. et al., *Am. J. Med. Sci.* 295: 453–458 (1988)), represent substantial advantages for the use of the mesothelial cells as target cells for human gene therapy.

Yet another viral candidate useful as an expression vector for transformation of mesothelial cells is the adenovirus, a double-stranded DNA virus. The adenovirus is frequently responsible for respiratory tract infections in humans and thus appears to have an avidity for the epithelium of the respiratory tract (Straus, S., *The Adenovirus*, H. S. Ginsberg, Editor, Plenum Press, New York, P. 451–496 (1984)). Moreover, the adenovirus is infective in a wide range of cell types, including, for example, muscle and endothelial cells (Larrick, J. W. and Burck, K. L., *Gene Therapy. Application of Molecular Biology*, Elsevier Science Publishing Co., Inc., N.Y., p. 71–104 (1991)). The adenovirus also has been used as an expression vector in muscle cells in vivo (Quantin, B., et al., *Proc. Natl. Acad. Sci. USA* 89: 2581–2584 (1992)).

Like the retrovirus, the adenovirus genome is adaptable for use as an expression vector for gene therapy, i.e., by removing the genetic information that controls production of the virus itself (Rosenfeld, M. A., et al., *Science* 252: 431–434 (1991)). Because the adenovirus functions in an extrachromosomal fashion, the recombinant adenovirus does not have the theoretical problem of insertional mutagenesis. However, because the adenovirus functions in an extra-chromosomal fashion, adenoviral transformation of a target mesothelial cell may not result in stable transduction.

Thus, as will be apparent to one of ordinary skill in the art, a variety of suitable viral expression vectors are available for transferring exogenous genetic material into mesothelial cells. The selection of an appropriate expression vector to express a therapeutic agent for a particular condition amenable to gene replacement therapy and the optimization of the conditions for insertion of the selected expression vector into the cell, are within the scope of one of ordinary skill in the art without the need for undue experimentation.

In an alternative embodiment, the expression vector is in the form of a plasmid, which is transferred into the target mesothelial cells by one of a variety of methods: physical (e.g., microinjection (Capecchi, M. R., *Cell* 22: 479–488 (1980)), electropotation (Andreason, G. L. and Evans, G. A. *Biotechniques* 6: 650–660 (1988), scrape loading, microparticle bombardment (Johnston, S. A., *Nature* 346: 776–777 (1990)) or by cellular uptake as a chemical complex (e.g., calcium or strontium co-precipitation, complexation with lipid, complexation with ligand) (Methods in Molecular Biology, Vol. 7, *Gene Transfer and Expression Protocols*, Ed. E. J. Murray, Humana Press (1991)). Several commercial products are available for cationic liposome complexation including Lipofectin(D (Gibco-BRL, Gaithersburg, Md.) (Felgner, P. L., et al., *Proc. Natl. Acad. Sci.* 84: 7413–7417 (1987)) and Transfectam® (ProMega, Madison, Wis.) (Behr, J. P., et al., *Proc. Natl. Acad. Sci. USA* 86: 6982–6986 (1989); Loeffler, J. P., et al., *J. Neurochem.* 54: 1812–1815 (1990)). However, the efficiency of transfection by these methods is highly dependent on the nature of the target cell and accordingly, the conditions for optimal transfection of nucleic acids into mesothelial cells using the above-mentioned procedures must be optimized. Such optimization is within the scope of one of ordinary skill in the art without the need for undue experimentation.

The instant invention also provides various methods for making and using the above-described genetically-modified mesothelial cells. In particular, the invention provides a method for genetically modifying n-tesothelial cell(s) of a mammalian recipient ex vivo and administering the genetically modified mesothelial cells to the mammalian recipient. In a preferred embodiment for ex vivo gene therapy, the mesothelial cells are autologous cells, i.e., cells isolated from the mammalian recipient. As used herein, the term "isolated" means a cell or a plurality of cells that have been removed from their naturally-occurring in vivo location. Methods for removing mesothelial cells from a patient, as well as methods for maintaining the isolated mesothelial cells in culture are known to those of ordinary skill in the art (Stylianou, E., et al., *Kidney Intl.* 37: 1563–1570 (1992); Hjelle, J. H., et al., *Peritoneal Dialysis Intl.* 9: 341–347 (1989); Heldin, P. *Biochem. J.* 283: 165–170 (1992); Di Paolo, N., et al., *Int. J. Art. Org.* 12: 485–501 (1989); Di Paolo, N., et al., *Clinical Nephrol.* 34: 179–1848 (1990); Di Paolo, N., et al., *Nephron* 57: 323–331 (1991)).

The instant invention also provides methods for genetically modifying mesothelial cells of a mammalian recipient in vivo. According to one embodiment, the method comprises introducing an expression vector for expressing a heterologous gene product into mesothelial cells of the mammalian recipient in situ by, for example, injecting the vector into a coelomic cavity of the recipient. In a preferred embodiment, the method comprises introducing a targeted expression vector, i.e., a vector having associated therewith a molecule that is specifically recognized by the target mesothelial cell. Such targeting is conferred to the vector by, for example, using a viral vector for targeting a mesothelial cell having on its surface viral receptors which specifically recognize and associate with the virus.

In a preferred embodiment, the preparation of genetically modified mesothelial cells contains an amount of cells sufficient to deliver a therapeutically effective dose of the therapeutic agent to the recipient in situ. The determination of a therapeutically effective dose of a specific therapeutic agent for a known condition is within the scope of one of ordinary skill in the art without the need for undue experimentation. Thus, in determining the effective dose, one of ordinary skill would consider the condition of the patient, the severity of the condition, as well as the results of clinical studies of the specific therapeutic agent being administered.

If the genetically modified mesothelial cells are not already present in a pharmaceutically acceptable carrier they are placed in such a carrier prior to administration to the recipient. Such pharmaceutically acceptable carriers include, for example, isotonic saline and other buffers as appropriate to the patient and therapy.

The genetically modified cells are administered by, for example, intraperitoneal injecting or implanting the cells or a graft or capsule containing the cells in a mesothelial cell-compatible site of the recipient. As used herein, "mesothelial cell-compatible site" refers to a structure, cavity or fluid of the recipient into which the genetically modified cell(s), mesothelial cell graft, or encapsulated mesothelial cell expression system can be implanted, without triggering adverse physiological consequences. Representative mesothelial cell-compatible sites include, for example, the peritoneal, pleural and pericardial cavities. Preferably, the mesothelial cell-compatible site communicates with the lymphatic system, thereby enabling delivery of the therapeutic agent to the vascular system.

In a preferred embodiment, the mesothelial cell-compatible site is denuded prior to implanting the cells. Exemplary denuding methods include but are not limited to: (1) injection of distilled water into the peritoneal cavity for 20 minutes, followed by scraping off a portion of the mesothelial layer; (2) injection of 0.1% buffered trypsin for 20 minutes followed by scraping; (3) removal of mesothelial cells by gentle scraping with a cell scraper and (4) touching a piece of Gelfilm (Upjohn, Kalamazoo, Mich.) to the mesothelium.

The genetically modified mesothelial cells are implanted in a mesothelial cell-compatible site, alone or in combination with other genetically modified mesothelial cells. Thus, the instant invention embraces a method for modifying the mesothelial system of a recipient by using a mixture of genetically modified mesothelial cells, such that a first modified cell expresses a first therapeutic agent and a second modified cell expresses a second therapeutic agent. Other genetically modified cell types (e.g., hepatocytes, smooth muscle cells, fibroblasts, glial cells, endothelial cells or keratinocytes) can be added, together with the genetically altered mesothelial cells, to produce expression of a complex set of introduced genes. Moreover, more than one recombinant gene can be introduced into each genetically modified cell on the same or different vectors, thereby allowing the expression of multiple therapeutic agents by a single cell.

The instant invention further embraces a mesothelial cell graft. The graft comprises a plurality of the above-described genetically modified cells attached to a support that is suitable for implantation into a mammalian recipient. The support can be formed of a natural or synthetic material. In another embodiment, the graft comprises a patch of peritoneum. Accordingly to this embodiment, the support is the naturally-occurring matrix that holds the plurality of genetically modified cells together. Alternatively, the graft comprises a plurality of the above-described cells attached to a substitute for the naturally occurring matrix (e.g., Gelfoam (Upjohn, Kalamazoo, Mich.), Dacron, Cortex®).

According to another aspect of the invention, an encapsulated mesothelial cell expression system is provided. The encapsulated system includes a capsule suitable for implantation into a mammalian recipient and a plurality of the above-described genetically modified mesothelail cells contained therein. The capsule can be formed of a synthetic or naturally-occurring material. The formulation of such capsules is known to one of ordinary skill in the art. In contrast to the mesothelial cells which are directly implanted into the mammalian recipient (i.e., implanted in a manner such that the genetically modified cells are in direct physical contact with the mesothelial cell-compatible site), the encapsulated cells remain isolated (i.e., not in direct physical contact with the site) following implantation. Thus, the encapsulated mesothelial system is not limited to a capsule including genetically-modified non-immortalize mesothelial cells, but may contain genetically modified immortalized mesothelial cells.

INTRODUCTION TO EXAMPLES

As described above, the present invention provides methods for forming a mesothelial cell expression system for expressing a heterologous gene product (e.g., a therapeutic agent) in a mammalian recipient, the expression system produced thereby and pharmaceutical compositions containing the same. The following Examples are directed to demonstrating the feasibility of mesothelial cell gene therapy in a rat model system (Examples, Part A), preliminary results demonstrating transfection of a human mesothelial cells in vitro, reimplantation of transformed mesothelial cells as xenografts into nude rats in vivo, and prophetic examples relating to the use of human mesothelial cells for gene therapy (Examples, Part B).

Briefly, the Examples demonstrate that rat mesothelial cells can be readily isolated from the peritoneum and expanded in vitro to large cell numbers. The cultured rat peritoneal mesothelial cells were transduced in vitro with a marker gene ($\beta$-galactosidase) using a retroviral vector and these transduced mesothelial cells were expanded in cell culture and reimplanted in syngeneic rat recipients. The reimplanted transduced cells continued to express $\beta$-galactosidase in vivo. The Examples also demonstrate that primary human mesothelial cells can be isolated, propagated in vitro, transfected with the gene for human growth hormone with attendant expression of the hormone by the transfected cells. These transfected human mesothelial cells implanted in nude rat recipients.

In the Examples, unless otherwise specified, restriction enzyme digests, ligations, transformations, and other routine procedures are performed as described in *Molecular Cloning, A Laboratory Manual* by Maniatis et al.

EXAMPLES

PART A

The feasibility of mesothelial cell gene therapy in a rat model system.

1. Transduction of a rat mesothelial cell line with BAG vector.

a. Stable transduction of a rat mesothelial cell line.

The *Escherichia coli* lacZ gene has been used as a convenient reporter gene because its product, $\beta$-galactosidase, can be readily detected in situ through the use of histochemical assays that stain the cytoplasm of the cell blue (Sanes, J. R. et al., *Embo J.* 5: 3133–3142 (1986)). 4/4RM.4, a rat pleural mesothelial cell line was transduced with the BAG virus (containing the genes for $\beta$-galactosidase and neomycin resistance) (Price, J. et al., *Proc. Natl Acad. Sci. USA* 84: 1560160 (1987)). This was accomplished by centrifugation concentration of virus from the conditioned medium from a producing culture of psi-2 BAG cells, and infecting subconfluent 4/4RM.4 cells with a mixture of the virus in Polybrene (Cepko, C. Lineage Analysis and Immortalization of Neural Cells via Retrovirus Vectors, in *Neuromethods*, Vol 16: Molecular Neurobiological Techniques, Boulton, A., Baker, G. B. and Campagnoni, A. T., editors, The Humana Press, Clifton, N.J. (1989), pp. 177–219). The cells were selected in G418 (a neomycin analog) to yield three sublines: MB1, MB2, MB3. Each of these sublines was analyzed for $\beta$-galactosidase activity by incubation with the $\beta$-galactosidase substrate 5-bromo-4-chloro-3-indolyl-$\beta$-D-galactoside (X-gal) (Cepko, C.,supra). From 50–70% of the cells in each subline showed positive staining (blue color) with MB3>MB2 >MB1. We then subcloned MB3 (using the cloning ring method) by picking eight colonies and screening each colony for $\beta$-galactosidase activity. We then selected three subclones, MB3.1, MB3.2 and MB3.3 for expansion. Further testing of subclones MB3.1, MB3.2 and MB3.3 indicated that >95% of the cells in each subclone demonstrated β-galactosidase activity (MB3.1>MB3.2 >MB3.3); and only a small percentage (3–5%) of the cells did not show any positive staining. Production of a blue color demonstrated the presence of β-galactosidase activity. Subclones MB3.2 and MB3.3 were frozen down and subclone MB3.1 expanded in large scale culture. These MB3.1 cells were used in initial reimplantation studies.

2. Reimplantation of transduced rat mesothelial cell line in vivo (Example Table 1 )

a. Time Course. MB3.1 cells were used in our initial studies on the reimplantation of transduced mesothelial cell into syngeneic Fisher rats. Experiments were of three types: 1) 6 animals received MB3.1 ($1\times10^7$ cells) i.p. These animals were sacrificed on days 2, 5, 7, 10, 14, 18 following reimplantation and at each time point the peritoneum was subjected to X-gal staining to determine if the MB3.1 cells were able to implant on the intact peritoneal surface. 2) 6 animals were treated surgically to open the abdominal wall along the midline. The peritoneal surface was wounded by touching a 2 cm$^2$ square piece of Gelfilm (Upjohn, Kalamazoo, Mich.) to the mesothelium thereby removing a section of mesothelial cells (Riese K. H., et al., Path, Res. Pract. 162: 327–336 (1978)). The peritoneal walls were then sutured closed and the animals received an injection of MB3.1 ($1\times10^7$ cells) i.p. These animals were sacrificed on days 2, 5, 7, 10, 14, and 18 after MB3.1 reimplantation and the peritoneum of each animal was subjected to X-gal staining to determine if MB3.1 cells preferentially implant on the denuded peritoneal surface and 3) 6 animals were treated surgically (wounded with Gelfilm) as above but did not receive MB3.1 cells, rather they received an injection of HBSS alone. These animals were sacrificed at the time points listed above and were subjected to X-gal staining to monitor mesothelial wound healing in the absence of MB3.1 cells. Subsequently, a second series of animals were wounded with Gelfilm and then received MB3.1 ($1\times10^7$ cells) i.p. These animals were sacrificed on days 21, 28, 35, 42, 49, 60 following reimplantation and the peritoneum of each rat was subjected to X-gal staining to analyze for expression of the reporter gene. Reimplantation of MB3.1 cells on a Gelfilm wounded peritoneal surface was performed as follows: $1\times10^7$ MB3.1 cells were injected i.p. 30 min. after surgery. Two days later, the animal was sacrificed, and the peritoneal wall excised. The tissue was fixed for 15 min in 0.5% glutaraldehyde, rinsed in PBS containing 2 mM $MgCl_2$ and stained with X-gal for 3 hr. As judged by the positive β-galactosidase staining (blue color), mesothelial cells reimplanted on the surface of the Gelfilm wounded area and along the mid-line incision but not on the normal (non-denuded) peritoneal surface. A portion of the peritoneal wall showing positive β-galactosidase staining (blue color), was dehydrated and embedded in paraffin. Four micron sections were cut, mounted and either stained with Hematoxylin & Eosin (H&E) or mounted without H&E staining. Transduced mesothelial cells that have attached to the peritoneal surface appeared as a turquoise blue monolayer. Macrophages expressing endogenous β-galactosidase activity were visible, as cells containing punctate-light blue staining, below the mesothelial surface. Further results of this series of reimplantation studies are summarized in Example Table 1. Taken together, these results indicate that the transduced mesothelial cells reimplant preferentially on a denuded peritoneal surface, and that expression of the reporter gene could be detected for at least two months.

Example TABLE 1

MB3.1 Reimplantation Studies in vivo - Results of X-gal Staining

| Treatment | Days after inoculation | | | | | | | | | | | |
|---|---|---|---|---|---|---|---|---|---|---|---|---|
| | 2 | 5 | 7 | 11 | 14 | 18 | 21 | 28 | 35 | 42 | 49 | 60 |
| I. MB3.1 No wound | – | – | – | – | – | ND | ND | ND | ND | ND | ND | ND |
| II. MB3.1 Gelfilm wound | ++ | ++ | ++ | ++ | ++ | ++ | – | ++ | – | – | ++ | + |
| III. Gelfilm wound only | +* | +* | +* | +* | – | ND | ND | ND | ND | ND | ND | ND |

Note:
– = no staining
++ = blue staining;
+* = macrophage staining;
ND = Not Determined.

Expression of β-galactosidase activity in Gelfilm-wounded animals was strongly positive for ~three weeks and then variable during the period from 28–60 days post implantation. We reasoned that this could be due to several possibilities: 1) lack of reimplantation of the MB3.1 mesothelial cells, 2) rejection of the implanted MB3.1 mesothelial cells or 3) successful reimplantation of the MB3.1 mesothelial cells followed by suppression of β-galactosidase gene expression in the reimplanted mesothelial cells. The expression of β-galactosidase activity on day 49 and 60 argued against rejection of the implanted mesothelial cells and argued against an abrupt turning off of the gent for β-galactosidase. Therefore we favored the first possibility. Our working hypothesis was that a lack of reimplantation of the transduced mesothelial cells is responsible for the observed lack of positive X-gal staining. The MB3.1 cells might fail to reimplant for several reasons; 1) the cells were not capable of binding to the denuded peritoneal surface, 2) the peritoneal wall had not been sufficiently denuded or 3) the cells were capable of binding to the denuded peritoneum, the peritoneal wall had been successfully denuded but titat too long a time had elapsed between denudation and reimplantation and the denuded peritoneum was no longer able to accept the mesothelial cells. We set about to investigate this further.

b. Comparison of various wounding protocols. To monitor the extent of mesothelial denudation, we investigated three additional types of wounds: 1) injection of distilled water into the peritoneal cavity for 20 min. followed by scraping off of a portion of the mesothelial layer, 2) injection of 0.1% buffered trypsin for 20 min. followed by scraping, and 3) removal of mesothelial cells by gentle scraping with a cell scraper. The animals were sacrificed three days after surgery and the peritoneal walls were removed and stained with X-gal. The results were as follows. Only the animal treated with trypsin showed any blue areas and these areas were minor in surface area. We repeated this experiment and this time both the trypsin-treated animals and the distilled water treated animal showed large blue areas stained positively for β-galactosidase. These inconsistent results led us to suspect that the cells were somehow not in the same condition prior to injection in each of the experiments.

c. Different time periods following trypsinization of MB3.1 cells:

Initially we had not been controlling for the amount of time that the MB3.1 cells sat on ice following trypsinization and removal from tissue culture but prior to injection into the animals following surgery and this time may have varied from 20 min. to 1½ hr. We began to control for the amount of time after surgery allowed to elapse before the MB3.1 cells were injected into the animals, and chose 30 min. as a reasonable and convenient time period. We performed the distilled water plus scraping treatment in two animals and then compared the reimplantation efficiency for cells that had been freshly prepared and injected into the denuded peritoneum 30 min following completion of surgery with cells that had been trypsinized, washed and left to sit on ice for 3½ hours before reimplantation in another rat 30 min after its surgery. Both animals were sacrificed 1 day after surgery and the peritoneal walls from both animals were removed and stained with X-gal. The results were quite dramatic in that only the animal injected with the freshly isolated mesothelial cells showed positive X-gal staining. From these results we concluded that MB3.1 cells left on ice for extended periods in HBSS no longer retain the ability to reimplant on a denuded peritoneal surface, although the exact reason remains obscure. However, we have modified our reimplantation procedure so that mesothelial cells are reimplanted in the peritoneal cavity immediately after trypsization.

d. Dose Response.

Four animals were treated surgically to open the abdominal wall along the midline. The peritoneal surface was wounded by touching a 2 cm² square piece of Gelfilm to the mesothelium thereby removing a small area of mesothelial cells. The peritoneal walls were then sutured closed and the animals received an i.p. injection of MB3.1 cells ($1\times10^7$, $1\times10^6$, $1\times10^5$, or $1\times10^4$ cells). These animals were sacrificed three days later and the peritoneal walls were subjected to X-gal staining to determine the number of MB3.1 cells required for implantation on the wounded peritoneal surface. Positive X-gal staining was observed in animals given $1\times10^7$ and $1\times10^6$ MB3.1 cells but not in animals given the lower doses of MB3.1 cells. Therefore we have used $5\times10^6$ cells as our injection dose in all subsequent reimplantation studies.

3. Isolation of rat primary peritoneal mesothelial cells (FIG. 1)

a. Isolation of rat primary mesothelial cells.

We constructed a plastic chamber device, based on a previously reported method (Hjelle, J. T. et al., *Perit. Dial. Int.* 9: 341–347 (1989)) to isolate the parietal peritoneal walls of Fisher rats ex vivo. Primary mesothelial cells were then removed from the excised parietal peritoneal wall using enzymatic treatment. Several different kinds of enzymatic treatment (2.5% trypsin, 0.05% collagenase, 2.5% trypsin-0.02% EDTA, 0.05% trypsin-0.02% EDTA) were compared with incubation periods varying from 5 to 90 min. Enzymatic digestion with 2.5% trypsin-0.02% EDTA for 60 min., followed by gentle scraping of the peritoneal wall surface with a cell scraper yielded a phenotypically pure population of cells that attached to the plastic tissue culture dishes within 12 to 24 hr. Rat primary peritoneal mesothelial cells were cuboidal, were contact inhibited and at confluence adopted a characteristic cobblestone appearance. The nuclei and nucleoli were visible.

b. In vitro culture of rat primary mesothelial cells.

Initial studies compared the effects of different growth media on the growth of rat peritoneal mesothelial cells. DME/F12, supplemented with either 10% calf serum or 15% fetal calf serum (FCS) appeared to be the best growth media for these rat primary mesothelial cells. FIG. 1 shows a growth curve for rat primary mesothelial cells. $1\times10^5$ cells were seeded in T25 flasks in DME/F12 supplemented with 15% FCS. The number of cells was determined daily by trypsinization and subsequent cell counting. Rat primary mesothelial cells cultured on tissue culture plastic reached a saturation density of $1\times10^5$ cells/cm² with a doubling time of ~24 h as shown in FIG. 1.

4. Characterization of rat primary mesothelial cells (Example Table 2)

a. Immunohistochemical staining of primary mesothelial cells and of MB3.1 cells. There are no markers that unequivocally identify mesothelial cells (Chung-Welch, N., et al., *Differentiation* 42: 44–53 (1989)). Isolated mesothelial cells were therefore subjected to immunohistochemical staining with a series of antibodies using fluorescein-conjugated double antibody technique as previously described (Hjelle, J. T. et al., *Perit. Dial. Int.* 9: 341–347 (1989)). Rat primary mesothelial cells, 4/4RM.4 cells and MB3.1 cells were compared with human unbiblical vein endothelial cells (HUVECs) obtained from Clonetics, San Diego, Calif.). The results are summarized in Example Table 2. All of the mesothelial cells were positive for cytokeratins 7, 8, 18 and 19 and vimentin and negative for a specific endothelial antigen. Taken together, these results indicate a pattern of staining for the primary mesothelial cells in agreement with previously published immunohistochemical results for mesothelial cells (Stylianou, E., et al., *Kid. Int.* 37: 1563–1570 (1990); Hjelle, J. T. et al., *Perit. Dial. Int.* 9: 341–347 (1989); and Wu, Y. J., et al., *Cell* 31: 693–703 (1982) and distinct from that observed for the HUVECs (Chung-Welch, N., et al., *Differentiation* 42: 44–53 (1989)).

b. Synthesis of matrix. Primary mesothelial cells were left to grow for extended periods after plating (2 weeks to 1 month) with weekly feeding. The cells remained contact inhibited but were observed to begin production and secretion of an extracellular matrix (Example Table 2). This matrix was analyzed by immunofluorescence staining with antibodies to a number of known extracellular matrix proteins. The results indicate that the major components of this matrix are fibronectin and laminin in agreement with previously published reports of extracelluar matrix production by mesothelial cells (Mackay, A. M., et al., *J. Cell Sci.* 95: 97–107 (1990) and Rennard, S. I. et al., *Am. Rev. Respir. Dis.* 130: 267–274 (1984)).

c. Uptake of DiI-AcLDL. The uptake of diI-AcLDL was analyzed in primary mesothelial cells and compared with uptake in human umbilical vein endothelial cells (HUVECs), commercially available from Clonetics, (San Diego, Calif.). The results were as follows: HUVECs appeared strongly positive indicating extensive uptake of diI-AcLDL, while primary n-tesothelial cells were only very weakly positive indicating only slight to moderate uptake.

d. Silver staining. 4/4RM.4 cells were grown to confluence and were stained using a $AgNO_3$ staining procedure (Joris, I. et al., Am. J. Pathol. 113: 341–358 (1983)) to produce deposits of silver, i.e. silver lines, at the mesothelial cell-mesothelial cell junctions. Results of confluent 4/4 RM.4 cell cultures were similar in appearance to the intact mesothelium (Fawcett, D. W. Bloom and Fawcett: A Textbook of Histology, 11th edition, W. B Saunders, Co. Philadelphia (1990), p.59) when stained ex vivo. Similar results were obtained with the rat primary mesothelial cells.

Example TABLE 2

Summary of Immunohistochemical Staining

| Antibody | Cell Type | | | |
|---|---|---|---|---|
| | 4/4 RM.4 | 1° Mesos | MB3.1 | HUVEC |
| anti-cytokeratin 8.12 | +/− | − | − | ND |
| anti-cytokeratin 8.13 | + | +/− | ND | ND |
| anti-cytokeratin 4.62 | +++ | +++ | +++ | +++ |
| anti-cytokeratin peptide 7 | +/− | +/− | ND | ND |
| anti-cytokeratin peptide 8 | +/− | +/− | ND | +/− |
| anti-cytokeratin peptide 13 | +/− | − | ND | ND |
| anti-cytokeratin peptide 14 | +/− | +/− | ND | ND |
| anti-cytokeratin peptide 18 | +/− | +/− | ND | ++ |
| anti-desmin | − | + | − | ND |
| anti-EGF receptor | − | +/− | ND | ND |
| CD31 endothelial cell | − | − | ND | +++ |
| A-CAM | +/− | +/− | ND | ND |
| anti-vimentin | +++ | +++ | +++ | +++ |
| anti-FVIII related antigen | + | + | ND | +++(WB) |
| anti-collagen I | +++ | +++ | +++ | ND |
| anti-collagen III | +++ | ++ | ++ | ND |
| anti-collagen IV | +++ | − | ++ | ND |
| anti-laminin | ++++ | +++ | ++++ | ND |
| anti-fibronectin | +++++ | ++++ | +++ | ND |
| anti-tenascin | + | ND | ND | ND |
| anti-entactin | ++ | − | ND | ND |

ND: not determined
WB: Weibel-Palade bodies e. Staining of primary mesothelial cell and HUVEC with FITC-phalloidin.

FITC-phalloidin was used to stain for actin filaments in primary mesothelial cells and in 4/4RM.4 cells at various stages of cell growth (pre-confluence to confluence) and in HUVECs. Peripheral bands of fluorescence were detected in the primary mesothelial cells prior to the induction of matrix. After the induction of matrix, the cells exhibited actin bundles more fibrillar in appearance.

5. Transduction of rat primary mesothelial cells in vitro.

a. Generation of stable transduced primary mesothelial cells. Rat primary mesothelial cells were transduced with BAG vector as follows: Conditioned medium from psi-2 BAG cells was centrifuged to remove cells and then filtered with 0.45 micron filter. This virus containing media was added to subconfluent rat primary mesothelial cells. The conditioned medium was changed 3 times over a one week period, and then the cells were subjected to selection by incubation in medium with G418. After approximately one month most of the primary cells died in the G418 selection media; however, several colonies appeared. Twenty colonies were transferred to duplicate 24-well plates, and when confluent tested for β-galactosidase activity. Three clones (#1, 14, and 15) were selected and expanded, and the X-gal staining process was repeated. Clone 14 stained the strongest for β-galactosidase activity. Greater than 95% of the Clone 14 cells stained blue, i.e., were positive for β-galactosidase. Therefore, Clone 14 was expanded for reimplantation studies.

6. Reimplantation of transduced rat primary mesothelial cells in vivo (Example Table 3)

a. Time Course and other wounding procedures. Transduced rat primary peritoneal mesothelial cells (Clone 14) were used for implantation studies. Initial studies paralleled our previous experiments with the MB3.1 transduced rat mesothelial cell line, but we also used the transduced rat primary mesothelial cells to investigate an alternative wounding procedure. In an attempt to optimize and streamline our surgical routine we compared the introduction and attachment of the primary mesothelial cells on peritoneal surfaces wounded by wetting with distilled water followed by scraping with a cell scraper, to attachment following injury induced by the Gelfilm (using the procedure discussed above). The results of these studies indicate that transduced rat primary mesothelial cells can attach to the peritoneal surface that has been denuded by either method (Example Table 3). We then carried out a time course study on autologous implantation of rat primary mesothelial cells transduced with BAG vector in Gelfilm wounded recipients. Representative results are shown in FIG. 5. A portion of the mesothelium covering the parietal peritoneal wall was removed by Gelfilm wounding. $5 \times 10^6$ rat primary mesothelial cells transduced with BAG vector (Clone 14) were injected j.p. immediately after surgery. From two to 47 days later, animals were sacrificed, and the peritoneal walls excised. Tissues were fixed for 15 min in 0.5% glutaraldehyde, rinsed in PBS containing 2 mM $MgCl_2$ and stained with X-gal for 3 hr. Photographs of whole mount of the stained peritoneal walls from rat sacrificed at various times after reimplantation were taken at 4, 14 and 21 days after reimplantation. As judged by the positive β-galactosidase staining (blue color), mesothelial cells reimplanted on the Gelfilm wounded surface and along the mid-line incision but not on the normal (non-denuded) peritoneal surface. Reimplanted transduced mesothelial cells continued to express the β-galactosidase transgene for at least 21 days.

Example TABLE 3

Rat Primary Mesothelial Cells Reimplantation Studies in vivo - Results of X-gal staining

| Treatment: | Days after inoculation | | | |
|---|---|---|---|---|
| | 1 | 2 | 5 | 7 |
| Distilled $H_2O$ + Scraping | ++ | ++ | ++ | ++ |
| Gelfilm wounding | ++ | ++ | ++ | ++ |

7. Transfection of rat primary mesothelial cells in vitro a. Strontium Phosphate In preliminary studies, we observed a striking toxic response of our rat primary mesothelial cells to calcium phosphate, thus precluding our use of calcium phosphate as a means to transfect rat mesothelial cells. To circumvent this difficulty, we used a modification of the traditional calcium phosphate transfection procedure to transfect the rat primary mesothelial cells. Previously, other workers have shown that, for primary cells showing sensitivity to calcium phosphate, a substitution of strontium phosphate for calcium phosphate allows stable transfection (Brash. D. E., et al. *Molec. Cell. Biol.* 7: 2031–2034 (1987)). We have used this strontium phosphate transfection protocol on the rat primary mesothelial cells. Our results (using pSVTKgH as reporter gene, see below) indicate positive transfection of rat primary mesothelial cells may be achieved by this method.

8. Significance of Preliminary Results.

Our preliminary studies in rat demonstrate that autologous mesothelial implants are likely to succeed, i.e. that mesothelial cells can be isolated, cultured and reimplanted without additional trauma, risk or side effects to the recipient. In addition, our initial studies with transduced mesothelial cells suggest that mesothelial cells may be good candidates for carriers of recombinant gene products in somatic-cell gene therapy.

PART B

Preliminary results relating to the isolation of human mesothelial cells, the transfection of human mesothelial cell in vitro and the reimplantation of transfected human mesothelial cells in vivo.

1. Isolation of primary human peritoneal mesothelial cells.

Human primary mesothelial cells were isolated from discarded surgical specimens (omentum) by trypsinization (Stylianou, E., et al., *Kidney Intl.* 37: 1563–1570 (1990); Pronk, A. et al. *In Vitro Cell. Dev. Biol.*, 29A: 127–134 (1993)). Human mesothelial cell were then grown in DME/F12, 15% FCS, L-glutamine, and antibiotics in the presence or absence of hydrocortisone (HC) and epidermal growth factor (EGF) (Rheinwald, J. G. "Methods for clonal growth and serial cultivation of normal epidermal keratinocytes and mesothelial cells", in *Cell Growth and Division: a practical approach*, Baserga, R., Editor, IRL Press, Oxford, England (1989), pp. 81–94). When human mesothelial cells were placed in tissue culture in media containing 5–10 ng/ml EGF and hydrocortisone (0.4 µg/ml), they grew rapidly, assured a quasi-fibroblastoid morphology and were not contact inhibited. However, when these mesothelial cells were deprived of EGF when the culture was ~50% confluent, the mesothelial cells slowed their growth rate substantially, became more flattened and stopped dividing when they reached a single cell monolayer, reminiscent of their in vivo morphology (Rheinwald, J. G., supra). Cultures of primary human mesothelial cells, grown in the presence of HC and EGF, were expanded at passages 2, 3, and 4 and frozen. We are presently analyzing the limits of primary human mesothelial cell survival in culture. Cells from our first donor began to deteriorate at about passage number 10, i.e., large, multi-nucleated cells appeared to dominate the culture, even in the presence of EGF. These results indicate that gene transfer transfection procedures must be initiated relatively quickly after cells are isolaized from the donor, preferably at passage 2–3.

2. Characterization of primary human mesothelial cells

Indirect immunofluorescence was used to confirm the identity of these human primary mesothelial cells. Human mesothelial cells (from passage 3 and from passage 8) stained positively with the following antibodies: anti-cytokeratin 19; anti-cytokeratin peptide 8; anti-cytokeratin peptide 18. These human mesothelial cells stained negatively with an anti-endothelial cell antigen (VWF) and with anti-desmin. Taken together, these results indicate a pattern of staining for the primary human mesothelial cells in agreement with previously published immunohistochemical results for mesothelial cells (Stylianou, E., et al., *Kid. Int.* 37: 1563–1570 (1990); Hjelle, J. T. et al., *Perit. Dial. Int.* 9: 341–347 (1989); and Wu, Y. J., et al., *Cell* 31: 693–703 (1982) and distinct from that observed for endothelial cells.

3. Transfection of human mesothelial cells with pSVT-Kgh. (Example Table 4)

pSVTKgH is a plasmid containing the gene for human growth hormone (gH) (Selden, R. F. et al., *Mol. Cell. Biol.* 6: 3173–3178, 1986). We have used pSVTKgH as a reporter to optimize the strontium phosphate transfection protocol on primary human mesothelial cells. We cotransfected mesothelial cells with supercoiled plasmids containing genes for growth hormone and neomycin resistance. Growth hormone expression was measured 2–3 days after the transfection by a solid-phase, two-site radioimmunoassay for human growth hormone using a commercially available kit (Nichols Institute Diagnostics, San Juan Capistrano, Calif.). This assay can detect as little as 0.2 ng of gH per milliliter, and is linear in the range of 0.2 to 50 ng/ml. Cotransfected human mesothelial cells were found to secrete detectable amounts of human growth hormone (Example Table 4). These positive populations of human mesothelial cells were subjected to selection in G418. Within several weeks several colonies appeared. These colonies were isolated and reanalyzed for secretion of growth hormone (Example Table 4). These data indicate that human mesothelial cells can be transfected with pSVTKgH to achieve transient expression of a transfected gene. Furthermore, a stable population of transfected human mesothelial cells has also been obtained using the strontium phosphate method. These cells were used for preliminary reimplantation studies in nude rats.

5. Implantation of pSVTKgh-transfected human mesothelial cells into Gelfilm wounded nude rats We used the human mesothelial cells, stably transfected with pSVTKgH by the strontium phosphate method (Brash. D. E., et al. *Molec. Cell. Biol.* 7: 2031–2034 (1987), to test for in vivo expression of the secreted gene product, growth hormone, in nude rats. In a pilot study, a pooled population of stably transfected human mesothelial cells, was labeled with the fluorescent cell tracker, DiO (Molecular Probes, Eugene, Oreg.), and reimplanted into a nude rat. This pilot study consisted of two nude rats: (1) a control animals (surgery, Gelfilm wound, no cells implanted) and (2) an experimental animal (surgery, Gel film wound, reimplantation of $1 \times 10^5$ pSVTKgH transfected, DiO-labelled human mesothelial cells). Expression of growth hormone was analyzed in peritoneal fluid and in the plasma. In this study, growth hormone analysis was performed on days 2, 5, 8 and 18 following implantation. On day 18, the experimental animal was sacrificed and the peritoneal wall was examined for the presence of DiO-labelled human mesothelial cells. Small patches of fluorescent cells were observed, scattered over the peritoneal surface. These results indicate that the transfected human mesothelial cells can implant on a denuded peritoneal surface and remain attached to that surface for at least 18 days.

Example TABLE 4

Strontium Phosphate Transfection of
Human Mesothelial Cells with SVTKgH

Experiment #1: Human mesothelial cells were grown in medium with egf/hc(+egf/hc). Cells assayed 1 day after removal of strontium phosphate precipitate; +/− glycerol shock.
Hgh RIA Results: Human Mesothelial Cells

| Hgh stds | cpm | −glycerol shock | cpm | +glycerol shock | cpm |
|---|---|---|---|---|---|
| 0 | 158 | 1 | 940 | 1 | 1719 |
| 5 ng/ml | 3239 | 2 | 670 | 2 | 5178 |
| | | 3 | 949 | 3 | 3453 |
| | | 4 | 614 | 4 | 3857 |

Results of Experiment #1: Human Mesothelial cells require glycerol shock for efficient transfection.

Experiment #2: Clones # 2, 3 and 4 + glycerol shock (above) were put into medium with G418 for selection (cells were cotransfected with pcDNAneo) + egf/hc and reassayed several days later.
Hgh RIA Results: Human Mesothelial Cells

| Hgh standards | cpm | Transfected Human Mesos | cpm |
|---|---|---|---|
| 0 | 231 | 2 | 17115 |
| 5 ng/ml | 7817 | 3 | 10085 |
| 50 ng/ml | 57483 | 4 | 14320 |

Results of Experiment #2: These data indicate successful transient transfection of human mesothelial cells.

Assay: RIA for hgh in mesothelial conditioned media using Nichols Institute Diagnostics Kit)

PART C

Figure 2:
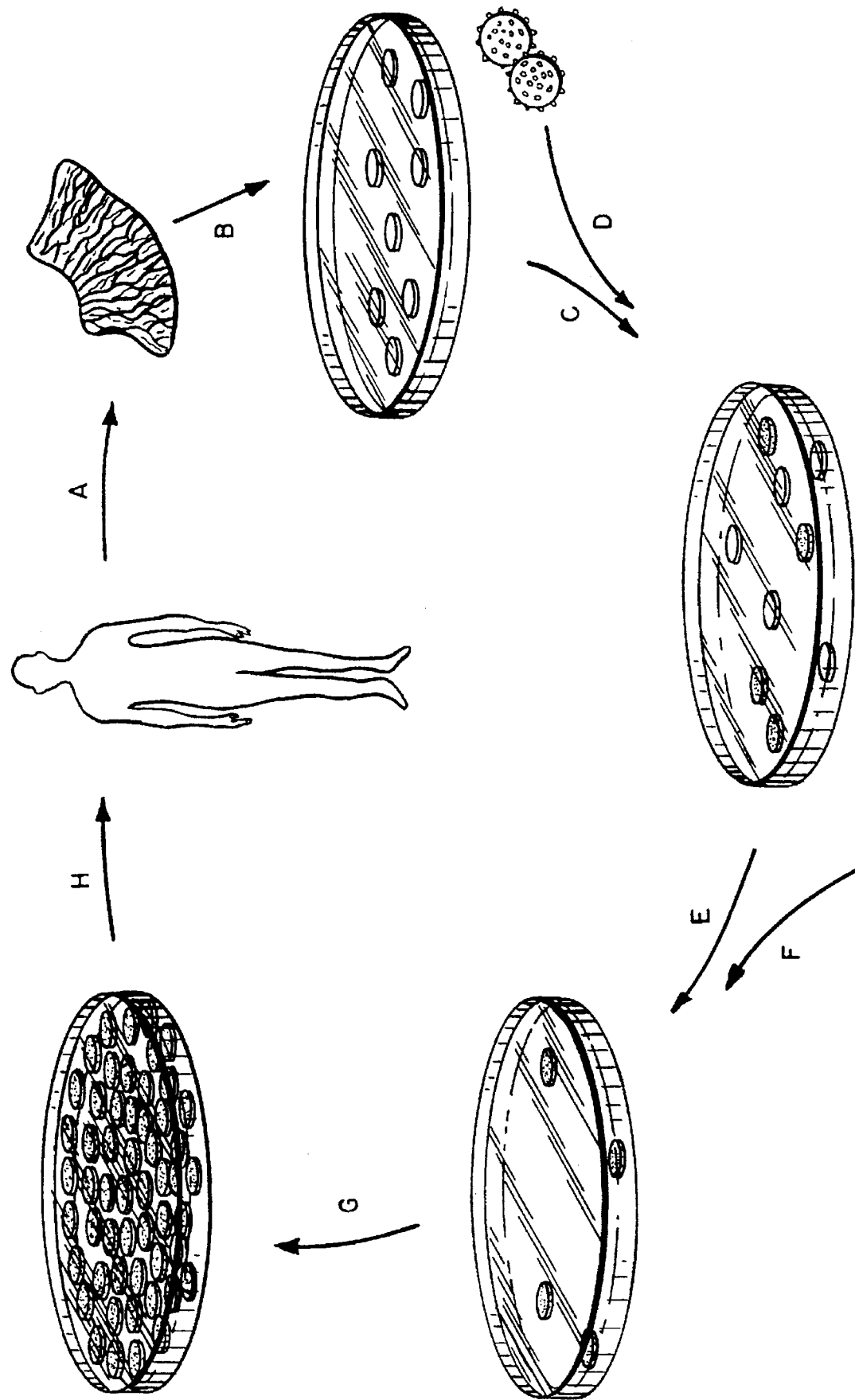
FIG. 2 is a schematic diagram of a method of human mesothelial cell gene therapy. The steps in the schematic diagram are: a) harvest omentum; b) isolate mesothelial cells; c) transduce with viral vector; d) retrovirus containing gene of interest; e) perform selection if desired; f) antibiotic (G418, neomycin); g) culture and characterize mesothelial cells; and h) implant.

Prophetic Example of human mesothelial cell gene therapy (FIG. 2)

A procedure for human gene therapy using genetically modified mesothelial cell is described herein. The preferred method utilizes autologous cells, i.e., cells that are isolated from the intended recipient of the genetically modified cells. The cells are harvested from the human donor by sampling the lining of a coelomic cavity, e.g. the surface of the omentum, according to methods known to one of ordinary skill in the art. Harvesting is performed at a time of surgical intervention or by laparoscopy. Thereafter, the harvested cells are established in cell culture according to methods known in the art for culturing mesothelial cells.

To prepare an expression vector for expressing a heterologous gene encoding a therapeutic agent, the gene is inserted into a replication-deficient retroviral vector according to methods known in the art. The heterologous gene preferably includes a constitutive promoter to permit transcription of the heterologous gene following its introduction into the mesothelial cell. Additional control elements, e.g. enhancers, are inserted into the heterologous gene according to standard methods to allow greater control of expression. Alternatively, inducible promoters are used to regulate transcription of the inserted gene. However, the use of inducible promoters further requires the step of exposing the genetically modified mesothelial cells to inducing agents in situ to achieve expression of the therapeutic agent in situ.

The expression system further includes a selectable marker (e.g., a marker for neomycin resistance) to facilitate selection of transduced mesothelial cells. The mesothelial cells are transduced in vitro with the above-described retroviral vector according to methods known in the art. Culture of the transduced mesothelial cells is performed in the presence of a selection medium (e.g., a medium neomycin) and the transduced cells are characterized. Only those transduced cells exhibiting stable expression of the therapeutic agent at a therapeutically effective level are selected for further characterization. The selected mesothelial cells are evaluated by immunohistochemical staining to determine whether the transduced cells are suitable for administration to the human recipient. Transduced cells suitable for direct administration to the recipient are non-immortalized and are non-tumorigenic. Additional characterization of the transduced cells is performed to establish that the cells comply with standards established by government agencies responsible for overseeing human gene therapy clinical trials.

Administration of the transduced mesothelial cells is by intraperitoneal injection of a suspension containing the cells into a coelomic cavity of the human recipient or by implanting the cells. Preferably, the site of implantation is denuded prior to implantation. For therapeutic agents which are directed to the systemic circulation, successful expression of the therapeutic agent in situ is evaluated by determining blood levels of the agent. In general, efficacy of the gene transfer therapy is determined by a reduction in clinical symptoms attributable to the condition for which the therapeutic agent is being administered.

It should be understood that the preceding is merely a detailed description of certain preferred embodiments. It therefore should be apparent to those skilled in the art that various modifications and equivalents can be made without departing from the spirit or scope of the invention.

What is claimed is:

1. A mesothelial cell expression system for expressing in a mesothelial cell of a mammalian recipient in vivo, a therapeutic agent for treating a condition, the expression system comprising:

a non-immortalized mesothelial cell from the same species as the mammalian recipient; and an expression vector contained therein for expressing the therapeutic agent, wherein said expression vector is useful for expressing the therapeutic agent in somatic cell types for human gene therapy, wherein the condition is treatable by local delivery of the therapeutic agent to a mesothelial cell-compatible site of the recipient and wherein the therapeutic agent is retained within or on the membrane of the non-immortalized mesothelial cell.

2. An expression system as claimed in claim 1, wherein the mammalian recipient is a human.

3. An expression system as claimed in claim 2, wherein said mesothelial cell is isolated from said human recipient.

4. An expression system as claimed in claim 3, wherein said mesothelial cell comprises a cell selected from the group consisting of a parietal mesothelial cell, a visceral surface mesothelial cell and a free-floating mesothelial cell.

5. An expression system as claimed in claim 4, wherein said mesothelial cell is isolated from the group consisting of a pleural cavity, a pericardial cavity and a peritoneal cavity.

6. The mesothelial cell expression system of claim 1, wherein said expression vector comprises a viral vector.

7. A pharmaceutical composition for local delivery of a therapeutic agent to a mesothelial cell-compatible site of a mammalian recipient, comprising:

a plurality of genetically modified non-immortalized mesothelial cells from the same species as the mammalian recipient, said cells containing an expression vector for expressing the therapeutic agent in the non-immortalized mesothelial cell, wherein the expression vector is useful for expressing the therapeutic agent in somatic cell types for human gene therapy; and a pharmaceutically acceptable carrier, wherein said therapeutic agent is for treating a condition that is treatable by local delivery of the therapeutic agent to the mesothelial cell-compatible site and wherein the therapeutic agent is retained within or on the membrane of the non-immortalized mesothelial cell.

8. The pharmaceutical composition of claim 7, wherein said expression vector comprises a viral vector.

9. A mesothelial cell graft, comprising, a support suitable for implantation into a mesothelial cell-compatible site of a mammalian recipient; and a plurality of genetically modified non-immortalized mesothelial cells attached to said support, wherein the genetically modified mesothelial cells are from the same species as the mammalian recipient and contain an expression vector for expressing in the genetically modified mesothelial cells a therapeutic agent for treating a condition that is treatable by local delivery of the therapeutic agent to the mesothelial cell-compatible site, wherein the therapeutic agent is retained within or on the membrane of the non-immortalized mesothelial cell and wherein the expression vector is useful for expressing the therapeutic agent in somatic cell types for human gene therapy.

10. The mesothelial cell graft of claim 9, wherein said expression vector comprises a vital vector.

11. An encapsulated mesothelial cell expression system, comprising, a capsule suitable for implantation into a non-immortalized mesothelial cell-compatible site of a mammalian recipient; and a plurality of genetically modified mesothelial cells contained within said capsule, wherein the genetically modified mesothelial cells are from the same species as the mammalian recipient and contain an expression vector for expressing in the genetically modified mesothelial cells a therapeutic agent for treating a condition that is treatable by local delivery of the therapeutic agent to the mesothelial cell-compatible site, wherein the therapeutic agent is retained within or on the membrane of the non-immortalized mesothelial cell and wherein the expression vector is useful for expressing the therapeutic agent in somatic cell types for human gene therapy.

12. The encapsulated mesothelial cell expression system of claim 11, wherein said expression vector comprises a viral vector.

13. A method for making a pharmaceutical preparation for administration to a mammalian recipient, the method comprising the steps of:

(a) introducing an expression vector for expressing a therapeutic agent into an isolated non-immortalized mesothelial cell to form a genetically modified mesothelial cell, wherein the mesothelial cell is from the same species as the mammalian recipient and wherein the expression vector is useful for expressing the therapeutic agent in somatic cells for human gene therapy; and (b) placing the genetically modified mesothelial cell in a pharmaceutically acceptable carrier to obtain a pharmaceutical preparation that is suitable for administration to a mesothelial cell-compatible site of the mammalian recipient, wherein the therapeutic agent is for treating a condition that is treatable by local delivery of the therapeutic agent to the mesothelial cell-compatible site and wherein the therapeutic agent is retained within or on the membrane of the non-immortalized mesothelial cell.

14. The method of claim 13, wherein the expression vector comprises a viral vector.

15. In a method for gene therapy, the improvement which comprises genetically modifying the mesothelial system of a mammalian recipient via the steps of introducing an expression vector for expressing in a mesothelial cell, a therapeutic agent into an isolated mesothelial cell to form a genetically modified mesothelial cell, wherein the non-immortalized isolated mesothelial cell is from the same species as the mammalian recipient, and wherein the expression vector is useful for expressing the therapeutic agent in somatic cell types for human gene therapy;

denuding a mesothelial cell-compatible site of the mammalian recipient; and administering said genetically modified mesothelial cell to the denuded mesothelial cell-compatible site of the mammalian recipient and allowing the genetically modified mesothelial cell to implant thereon, wherein the mammalian recipient has a condition that is treatable by local delivery of the therapeutic agent to the mesothelial cell-compatible site or by administration of the therapeutic agent to the systemic circulation.

16. A method as claimed in claim 15, wherein said mesothelial cell is isolated from the mammalian recipient.

17. A method as claimed in claim 15, wherein administering said genetically modified cell comprises injecting said genetically modified cell into said mammalian recipient.

18. A method as claimed in claim 15, wherein administering said genetically modified mesothelial cell comprises implanting said genetically modified cell into a mesothelial cell-compatible site of the mammalian recipient.

19. A method as claimed in claim 15, wherein administering said genetically modified mesothelial cell comprises implanting a mesothelial cell graft including a plurality of said genetically modified cells attached to a support.

20. A method as claimed in claim 15, wherein administering said genetically modified mesothelial cell comprises implanting an encapsulated mesothelial cell expression system including a plurality of said genetically modified cells contained within a capsule suitable for implantation into the mammalian recipient.

21. A method as claimed in claim 15, wherein said expression vector further includes an inducible promoter for controlling transcription of said therapeutic agent said method further comprising the step of exposing the genetically modified mesothelial cell in situ to conditions for permitting transcription of the therapeutic agent.

22. The method of claim 15, wherein the expression vector comprises a viral vector.

23. The method of claim 15, wherein the mammalian recipient is a human.

24. The method of claim 15, wherein the condition is treatable by local delivery of the therapeutic agent to the mesothelial cell-compatible site.

25. The method of claim 15, wherein the therapeutic agent is retained within or on the membrane of the non-immortalized mesothelial cell.

* * * * *

UNITED STATES PATENT AND TRADEMARK OFFICE
CERTIFICATE OF CORRECTION

PATENT NO. : 5,645,829
DATED : July 8, 1997
INVENTOR(S) : Ty Robert Shockley, Robert William Jackman, Janice Ann Nagy It is certified that error appears in the above-identified patent and that said Letters Patent is hereby corrected as shown below:

Column 4, line 5 please change "in .situ" to --in situ--.
Column 10, line 11 please change "a functionally" to --functionally--.
Column 11, line 10 please change "ascites" to --ascite--.
Column 11, line 52 please change "agene" to --a gene--.
Column 16, line 9 please change "n-tesothelial" to --mesothelial--.
Column 18, line 6 please change "a human" to --human--.
Column 22, line 39 please change "unbiblical" to --umbilical--.
Column 22, line 44 please change "antigert" to --antigen--.
Column 23, line 4 please change "n-tesothelial" to --mesothelial--.
Column 24, line 32 please change "j.p." to --i.p.--.
Column 24, line 38 please change "rat" to --rats--.
Column 25, line 34 please change "cell" to --cells--.
Column 25, line 35 please change "L-Glutarnine" to --L-Glutamine--.
Column 25, line 62 please change "isolaized" to --isolated--.
Column 26, line 15 please change "Kgh" to --KgH--.
Column 26, line 44 please change "pSVTKgh" to --pSVTKgH--.
Column 26, line 45 please add a period at the end of sentence after the word "rats".
Column 26, line 55 please change "animals" to --animal--.
Column 29, line 13 please change "graff" to --graft--.
Column 29, line 30 please change "vital" to --viral--.

Signed and Sealed this

Third Day of March, 1998

Attest:

BRUCE LEHMAN

Attesting Officer

Commissioner of Patents and Trademarks